US010221131B2

(12) United States Patent
Kaur et al.

(10) Patent No.: US 10,221,131 B2
(45) Date of Patent: Mar. 5, 2019

(54) ACID GENERATOR COMPOUNDS AND PHOTORESISTS COMPRISING SAME

(71) Applicant: Rohm and Haas Electronic Materials LLC, Marlborough, MA (US)

(72) Inventors: Irvinder Kaur, Marlborough, MA (US); Cong Liu, Marlborough, MA (US); Cheng-Bai Xu, Marlborough, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 15/167,223

(22) Filed: May 27, 2016

(65) Prior Publication Data

US 2016/0347709 A1    Dec. 1, 2016

Related U.S. Application Data

(60) Provisional application No. 62/169,402, filed on Jun. 1, 2015.

(51) Int. Cl.
| G03F 7/004 | (2006.01) |
| C07C 309/17 | (2006.01) |
| C07D 307/00 | (2006.01) |
| C07D 493/18 | (2006.01) |
| C07C 381/12 | (2006.01) |
| H01L 21/027 | (2006.01) |
| C07C 309/01 | (2006.01) |
| G03F 7/039 | (2006.01) |

(52) U.S. Cl.
CPC .......... *C07C 309/17* (2013.01); *C07C 309/01* (2013.01); *C07C 381/12* (2013.01); *C07D 307/00* (2013.01); *C07D 493/18* (2013.01); *G03F 7/0045* (2013.01); *G03F 7/0046* (2013.01); *G03F 7/0397* (2013.01); *H01L 21/0274* (2013.01); *C07C 2601/14* (2017.05); *C07C 2603/74* (2017.05)

(58) Field of Classification Search
CPC ... G03F 7/004; G03F 7/26; G03F 7/40; C07C 381/12; C07C 309/01; C07C 309/17; H01L 21/0274
USPC ............ 430/370.1, 322, 314, 270.1; 558/44; 562/125; 568/18
See application file for complete search history.

(56) References Cited

U.S. PATENT DOCUMENTS

| 8,889,333 | B2* | 11/2014 | Ichikawa | C07C 309/12 |
| | | | | 430/270.1 |
| 9,034,556 | B2* | 5/2015 | Hada | C07C 309/17 |
| | | | | 430/270.1 |
| 9,221,785 | B2* | 12/2015 | Ichikawa | C07C 309/17 |
| 9,346,750 | B2* | 5/2016 | Ichikawa | C07C 309/17 |
| 9,562,032 | B2* | 2/2017 | Masuyama | C07D 319/08 |
| 2007/0100096 | A1 | 5/2007 | Harada et al. | |
| 2008/0008942 | A1 | 1/2008 | Yin et al. | |
| 2010/0248135 | A1* | 9/2010 | Masuyama | G03F 7/0046 |
| | | | | 430/270.1 |
| 2011/0020749 | A1 | 1/2011 | Ichikawa et al. | |
| 2011/0117493 | A1 | 5/2011 | Ichikawa et al. | |
| 2011/0117495 | A1 | 5/2011 | Ichikawa et al. | |
| 2012/0009521 | A1* | 1/2012 | Kawaue | C07C 309/09 |
| | | | | 430/281.1 |
| 2013/0122424 | A1 | 5/2013 | Yamashita et al. | |
| 2015/0338736 | A1* | 11/2015 | Kawabata | C07C 309/17 |
| | | | | 430/281.1 |

FOREIGN PATENT DOCUMENTS

| JP | 2012006911 A | * | 1/2012 | |
| JP | 2012176936 A | * | 9/2012 | |
| JP | 2013092618 A | * | 5/2013 | |
| JP | 2013126968 A | * | 6/2013 | |
| JP | 2014040405 A | * | 3/2014 | |
| JP | 2014167611 A | * | 9/2014 | |
| JP | 2016153409 A | * | 8/2016 | ........... C07C 309/17 |

OTHER PUBLICATIONS

English language summary of Office Action issued in counterpart Japanese Application 2016-099460.
English language summary of Office Action issued in counterpart Chinese Application No. 201610380432.9.
English language summary of Office Action dated Nov. 20, 2017 issued in counterpart Korean Application No. 10-2016-0067394.

* cited by examiner

*Primary Examiner* — Amanda C. Walke
(74) *Attorney, Agent, or Firm* — Mintz Levin Cohn Ferris Glovsky and Popeo, P.C.; Peter F. Corless

(57) ABSTRACT

Acid generator compounds are provided that are particularly useful as a photoresist composition component. In one preferred aspect, acid generators are provided that comprise one or more hydrophilic moieties.

18 Claims, No Drawings

ACID GENERATOR COMPOUNDS AND PHOTORESISTS COMPRISING SAME

CROSS REFERENCE TO RELATED APPLICATION

This application claims the benefit of U.S. Provisional Application No. 62/169,402, filed Jun. 1, 2015, the disclosure of which is hereby incorporated by reference herein in its entirety.

FIELD

The present invention relates to new acid generator compounds. In one preferred aspect, acid generators are provided that comprise one or more hydrophilic moieties.

INTRODUCTION

Photoresists are photosensitive films for transfer of images to a substrate. They form negative or positive images. After coating a photoresist on a substrate, the coating is exposed through a patterned photomask to a source of activating energy such as ultraviolet light to form a latent image in the photoresist coating. The photomask has areas opaque and transparent to activating radiation that define an image desired to be transferred to the underlying substrate. A relief image is provided by development of the latent image pattern in the resist coating.

Known photoresists can provide features having resolution and dimension sufficient for many existing commercial applications. However for many other applications, the need exists for new photoresists that can provide highly resolved images of submicron dimension.

Various attempts have been made to alter the make-up of photoresist compositions to improve performance of functional properties. Among other things, a variety of photoactive compounds have been reported for use in photoresist compositions. See U.S. patent applications US 20110020749; US 20110117493; US 20070100096; and US 20070100096.

Scumming is a notable issue that can limit photoresist resolution. This occurs where photoresist material remains on a substrate in areas intended to be bared of resist through development (i.e., in the case of a positive resist, photoresist material remains in exposed regions following development). Such resist scum can cause fabrication failures. See US 20080008942.

It thus would be desirable to have new photoresist compositions. It also would be desirable to have photoresist compositions that could exhibit reduced scumming.

SUMMARY

We have now discovered new acid generator compounds particularly useful as a photoresist composition component. Preferred acid generators comprise one or more hydrophilic moieties.

In a preferred aspect, acid generators are provided that comprise a structure of the following Formula (I):

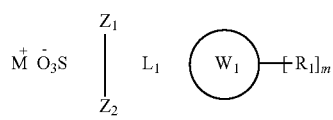
(I)

wherein in Formula (I):
$M^+$ is a counter ion;
$Z_1$ and $Z_2$ each independently represent a hydrogen or non-hydrogen substituent, where at least one of $Z_1$ or $Z_2$ is fluorine or fluoroalkyl;
$L_1$ is a linker group;
$W_1$ is an optionally substituted carbon alicyclic group or optionally substituted heteroalicyclic group;
$R_1$ is —(C=O)O(—(CXY)(CX'Y')O)$_n$R where n is a positive integer, R is optionally substituted alkyl, optionally substituted alkoxy, hydrogen or hydroxyl, each X, Y, X' and Y' is independently the same or different hydrogen or non-hydrogen substituent; and
m is a positive integer.

In one preferred aspect, in Formula (I), $W_1$ is an optionally substituted heteroalicyclic group such as an optionally substituted lactone.

In another aspect, in Formula (I), $W_1$ is an optionally substituted carbon alicyclic group.

In a preferred aspect, acid generators are provided that comprise a structure of the following Formula (Ia):

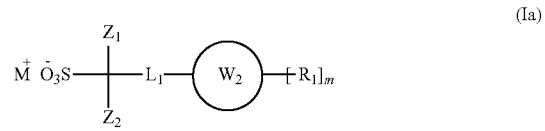
(Ia)

wherein in Formula (Ia):
$M^+$ is a counter ion;
$Z_1$ and $Z_2$ each independently represents a hydrogen or non-hydrogen substituent, where at least one of $Z_1$ or $Z_2$ is fluorine or fluoroalkyl;
$L_1$ is a linker group;
$W_2$ is an optionally substituted cycloalkyl group or optionally substituted heterocycloalkyl group;
$R_1$ is —(C=O)O(—(CXY)(CX'Y')O)$_n$R where n is a positive integer, R is optionally substituted alkyl, optionally substituted alkoxy, hydrogen or hydroxyl, each X, Y, X' and Y' is independently the same or different hydrogen or non-hydrogen substituent;
m is a positive integer.

In one preferred aspect, in Formula (Ia), $W_2$ is an optionally substituted cycloalkyl group such as an optionally substituted cyclohexane.

In one preferred aspect, in Formula (Ia), $W_2$ is an optionally substituted heterocycloalkyl group such as an optionally substituted lactone, piperidine, oxane or thiane.

In a preferred aspect, acid generators are provided that comprise a structure of the following Formula (Ib):

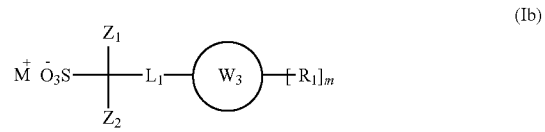
(Ib)

wherein in Formula (Ib):
$M^+$ is a counter ion;
$Z_1$ and $Z_2$ each independently represents a hydrogen or non-hydrogen substituent, where at least one of $Z_1$ or $Z_2$ is fluorine or fluoroalkyl;
$L_1$ is a linker group;
$W_3$ is an optionally substituted polycycloalkyl group or optionally substituted polyheterocycloalkyl group;
$R_1$ is a group of the following formula: —(C=O) O(—(CXY)(CX'Y')O)$_n$R where n is a positive integer, R is optionally substituted alkyl, optionally substituted alkoxy, hydrogen or hydroxyl, each X, Y, X' and Y' is independently the same or different hydrogen or non-hydrogen substituent;

m is a positive integer.

In one preferred aspect, in Formula (Ib), $W_3$ is an optionally substituted polycycloalkyl group such as an optionally substituted decalin, norbornane or adamantane.

In another preferred aspect, in Formula (Ib), $W_3$ is an optionally substituted polycycloalkyl group or optionally substituted polyheterocycloalkyl group;

Preferably, in the above Formulae (I), (Ia) and (Ib), in the group —(C=O)O(—(CXY)(CX'Y')O)$_n$R (i.e. $R_1$), n is 5 or less, and more preferably n is 1, 2 or 3, and in particular embodiments n is 1 or 2.

Preferably, in the above Formulae (I), (Ia) and (Ib), in the group —(C=O)O(—(CXY)(CX'Y')O)$_n$R (i.e. an $R_1$ group), one or more of X, Y, X' and Y' is hydrogen, including where each of X, Y, X' and Y' is hydrogen, i.e. where $R_1$ is —(C=O)O(—CH$_2$CH$_2$O)$_n$R, including where n is 5 or less, and more preferably n is 1, 2 or 3, and in particular embodiments n is 1 or 2, especially 2.

Preferably, in the above Formulae (I), (Ia) and (Ib), m is 5 or less, and more preferably m is 1, 2 or 3, and in particular embodiments m is 1 or 2.

Preferably, in the above Formulae (I), (Ia) and (Ib), both $Z_1$ and $Z_2$ are fluorine or fluoroalkyl.

Preferably, in the above Formulae (I), (Ia) and (Ib), various W groups ($W_1$, $W_2$, or $W_3$) may be optionally substituted lactone, optionally substituted cyclohexane or optionally substituted adamantane.

$L_1$ suitably contains one or more carbon atoms, typically 1 to about 4, 5, 6, 7, 8, 9 or 10 carbon atoms and may comprise an alkyl group, ether group, ester group, amide group, or sulfonate groups. In certain aspects, $L_1$ comprises an ester group, e.g. —(CX"Y")$_m$(C=O)O— where m is 0, 1, 2, 3, 4, 5, or 6, and each X" and Y" is halogen particularly fluorine, optionally substituted $C_{1-8}$alkyl, particularly $C_{1-6}$fluoroalkyl such as $CF_3$, or hydrogen.

A variety of cation components ($M^+$) may be suitably employed. In one preferred aspect, M+ comprises a sulfonium group.

In certain preferred aspects, an acid generator of the invention may be covalently linked to a polymer. Such polymer may be suitably utilized as a component of a photoresist composition. The polymer may comprise acid-labile groups in addition to the covalently linked acid generator compounds. In such aspects, suitably the anion component but not the cation component of an ionic acid generator compound of the invention may be covalently linked to a polymer, or the cation component but not the anion component of the acid generator may be covalently linked to a polymer, or each of the anion and cation components of the acid generator may be covalently linked to a polymer.

Without being bound by theory, it is believed that use of such bulky-moiety acid-labile groups can enhance lithographic performance of a photoresist comprising the acid generator compound, including by providing enhanced contrast relative to a comparable system that does not include such bulky moieties.

Particularly preferred photoresists of the invention may comprise an imaging-effective amount of one or more acid generator compounds as disclosed herein and a suitable polymer component. Photoresists of the invention also may comprise a mixture of distinct acid generator compounds, typically a mixture of 2 or 3 different acid generator compounds, more typically a mixture that consists of a total of 2 distinct acid generator compounds.

In another aspect, methods for synthesizing an acid generator of the invention are provided. In one preferred embodiment, such methods may comprise reacting an unsaturated anhydride with a hydroxy-alkoxy agent to provide an unsaturated substituted lactone; and functionalizing the lactone to provide the acid generator.

Methods are also provided for forming relief images of photoresist compositions of the invention (including patterned lines with sub sub-50 nm or sub-20 nm dimensions). Such methods may comprise, for example: a) applying a coating layer of a photoresist of the invention on a substrate; b) exposing the photoresist composition layer to activating radiation; and c) developing the exposed photoresist composition coating layer.

Substrates such as a microelectronic wafer also are provided having coated thereon a photoresist composition of the invention.

Other aspects of the invention are discussed infra.

DETAILED DESCRIPTION

Acid Generator Compounds

As referred to herein, acid generator compounds can produce an acid when exposed to activating radiation, such as 193 nm wavelength radiation and other radiation sources such as EUV radiation and e-beam radiation. Acid generator compounds as referred to herein also may be referred to as photoacid generator compounds.

We have found that certain ionic acid generators that have large anion component can result in scum production (post-development residual resist material) on the substrate surface of developed exposed resist layer regions. Without being bound by any theory, we consider that such undesired scumming may result from slow diffusion of the bulky hydrophobic anion component to bottom regions of a resist layer prior to development. While slow diffusion of the anion component can be advantageous in part because it reduces the amount of photogenerated-acid undesirably moving into unexposed resist layer regions which can reduce resolution, we believe such slow diffusion can also result in undesired scumming.

We have now found that incorporating one or more certain hydrophilic groups into an acid generator that has a large anion component can simultaneously result in desired low diffusivity but with reduced undesired post-development scumming Again without being bound by theory, it is believed the anion component's hydrophilic group(s) can promote migration of the anion component to bottom regions of the exposed resist layer which can lead to scum reduction.

Acid Generator Compounds

As discussed above, preferred acid generator compounds include those of Formulae (I), as defined above.

In the above Formulae (I), suitable non-hydrogen substituents, may be e.g. halo (F, Cl, Br or I); cyano, nitro, hydroxy, optionally substituted C1-20alkyl, optionally substituted C1-20alkoxy, such as optionally substituted alkyl (e.g. optionally substituted C1-10 alkyl), optionally substituted alkenyl or alkynyl preferably having 2 to about 20 carbon atoms such as such as allyl; optionally substituted ketones preferably having 1 to about 20 carbon atoms; optionally substituted alkylthio preferably having 1 to about 20 carbon atoms; optionally substituted alkylsulfinyl preferably 1 to about 20 carbon atoms; optionally substituted alkylsulfonyl preferably having 1 to about 20 carbon atoms; optionally substituted carboxy preferably have 1 to about 20 carbon atoms (which includes groups such as —COOR' where R' is H or C1-8alkyl, including esters that are substantially non-reactive with photoacid); optionally substituted alkaryl such as optionally substituted benzyl, optionally substituted carbocyclic aryl such as optionally substituted phenyl, naphthyl, acenaphthyl, or optionally substituted heteroalicyclic or heteroaromatic group such as pyridyl, furanyl, pyrrole, thiophene, furan, imidazole, pyrazole, oxazole, isoxazole, thiazole, isothiazole, triazole, furanzan, oxadiazole, thiadiazole, dithiazole, terazole, pyran, thiopyran, diazine, oxazine, thiazine, dioxine, dithine, and triazine and polyaromatic groups containing one or more of such moieties.

As discussed above, various W groups ($W_1$, $W_2$, or $W_3$) suitably may be an optionally substituted carbon alicyclic group, optionally substituted cycloalkyl group or an optionally substituted polycycloalkyl. As referred to herein, the term "carbon alicyclic group" means each ring member of the non-aromatic group is carbon. The carbon alicyclic group can have one or more endocyclic carbon-carbon double bonds, provided the ring is not aromatic. The term optionally substituted "cycloalkyl group" means each ring member of the non-aromatic group is carbon and the carbon ring does not have any endocyclic carbon-carbon double bonds. For instance, cyclohexyl, cyclopentyl and adamantyl are cycloalkyl groups as well as carbon alicyclic groups. The term "optionally substituted polycycloalkyl" means a cyclocalkyl group that has multiple (e.g. 2, 3, 4 or more) fused, bridged or otherwise covalently linked cycloalkyl groups. For instance, adamantyl is a polycycloalkyl group. Carbon alicyclic groups and cycloalkyl groups may comprise one ring or multiple (e.g. 2, 3, 4 or more) bridged, fused or otherwise covalently linked rings.

Various W groups ($W_1$, $W_2$, or $W_3$) suitably also may be an optionally substituted carbon heteroalicyclic group, optionally substituted heterocycloalkyl group or an optionally substituted polyheterocycloalkyl. As referred to herein, the term "heteroalicyclic group" means the non-aromatic ring group has at least one ring member other than carbon, typically at least one O, N or S ring atom, and in particular embodiments at least one oxygen ring member. The heteroalicyclic group can have one or more endocyclic double bonds, provided the ring is not aromatic. The term optionally substituted "heterocycloalkyl group" means means the non-aromatic ring group has at least one ring member other than carbon, typically at least one O, N or S ring atom (and in particular embodiments at least one oxygen ring member) and that the ring does not have any endocyclic double bonds. The term "optionally substituted polyheterocycloalkyl" means a heterocyclocalkyl group that has multiple (e.g. 2, 3, 4 or more) fused, bridged or otherwise covalently linked heterocycloalkyl groups. For instance, a bridged lactone groups is a polyheterocycloalkyl group. Heteroalicyclic groups and heterocycloalkyl groups may comprise one ring or multiple (e.g. 2, 3, 4 or more) bridged, fused or otherwise covalently linked rings.

As discussed, various moieties of acid generator compounds and other materials may be optionally substituted. A "substituted" substituent may be substituted at one or more available positions, typically 1, 2, or 3 positions by one or more suitable groups such as e.g. halogen (particularly F, Cl or Br); cyano; nitro; $C_{1-8}$ alkyl; $C_{1-8}$ alkoxy; $C_{1-8}$ alkylthio; $C_{1-8}$ alkylsulfonyl; $C_{2-8}$ alkenyl; $C_{2-8}$ alkynyl; hydroxyl; nitro; alkanoyl such as a $C_{1-6}$ alkanoyl e.g. acyl, haloalkyl particularly $C_{1-8}$ haloalkyl such as $CF_3$; —CONHR, —CONRR' where R and R' are optionally substituted $C_{1-8}$alkyl; —COOH, COC, >C=O; and the like.

As discussed above, the cation component ($M^+$) of an acid generator suitably may be selected from a variety of groups, including iodonium and sulfonium components, with sulfonium being preferred in many aspects. Organic cations are also typically preferred.

Specifically preferred cations ($M^+$ in formula (I)) include the following:

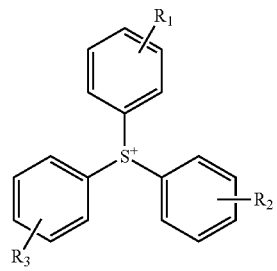

C

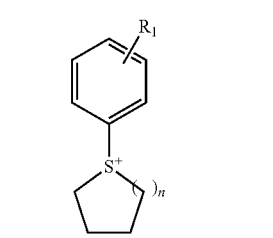

D n = 1, 2, 3, 4, 5, 6, 7, 8, 9, 10

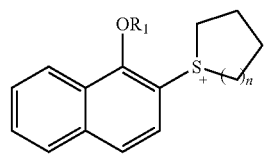

E n = 1, 2, 3, 4, 5, 6, 7, 8, 9, 10

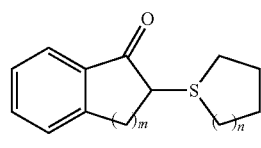

F n = 1, 2, 3, 4, 5, 6, 7, 8, 9, 10
m = 1, 2

Specifically preferred acid generator compounds include those having one or more of the following cation components:

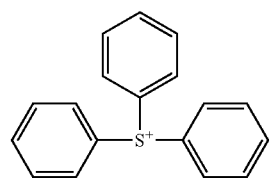

C1

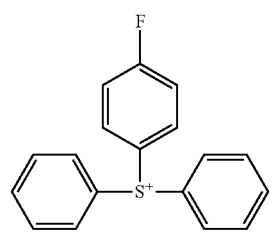

C2

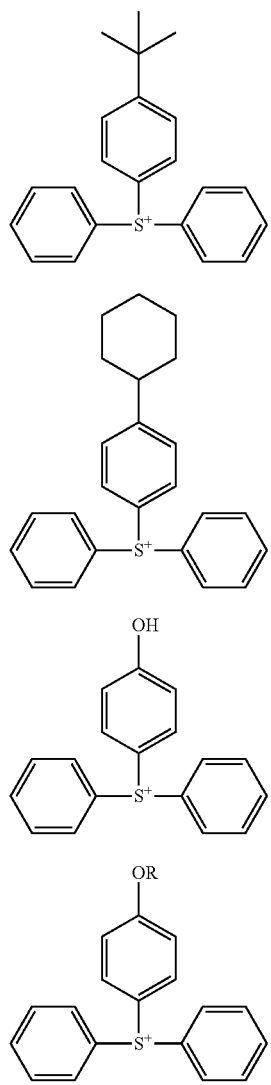
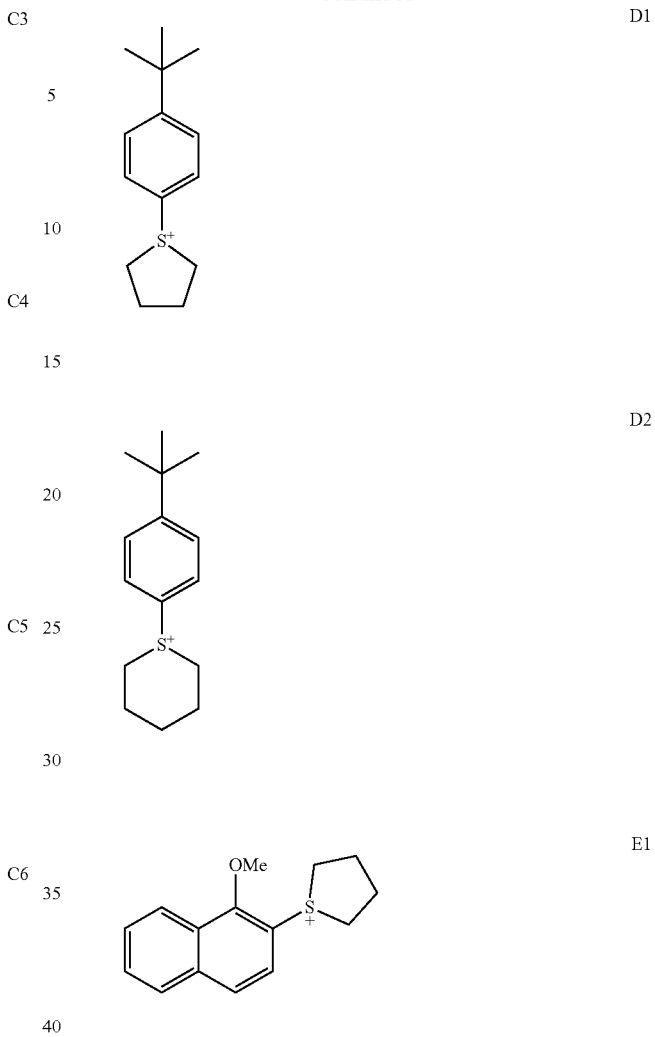
Specifically preferred acid generators include the following where M+ is a cation component as discussed herein with respect to Formula (I)
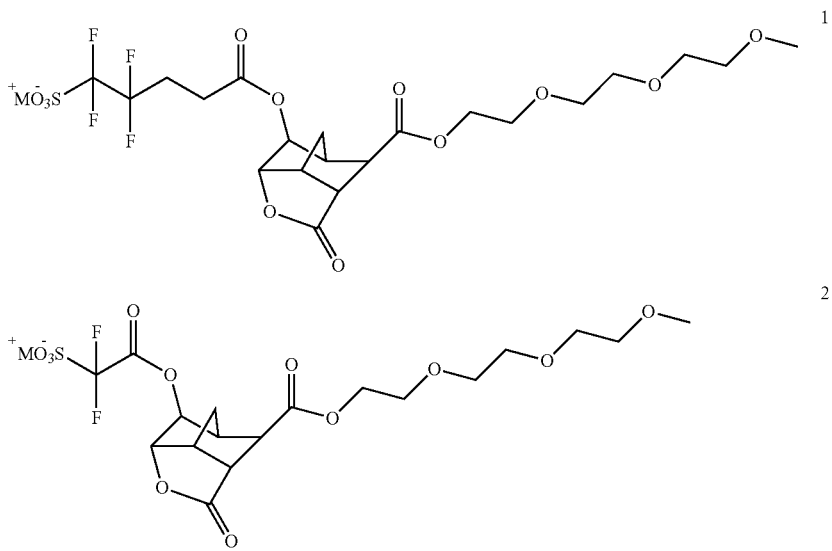

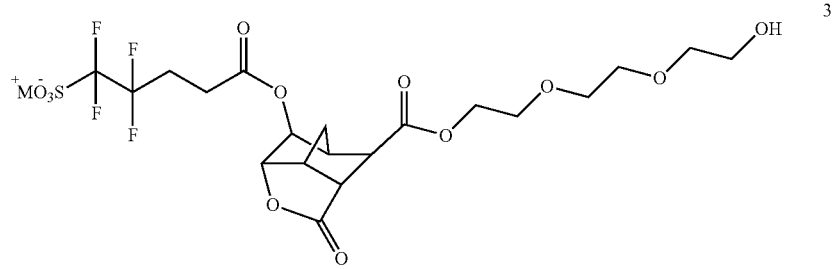
3
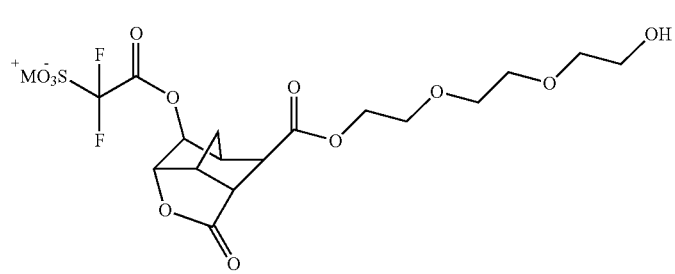
4
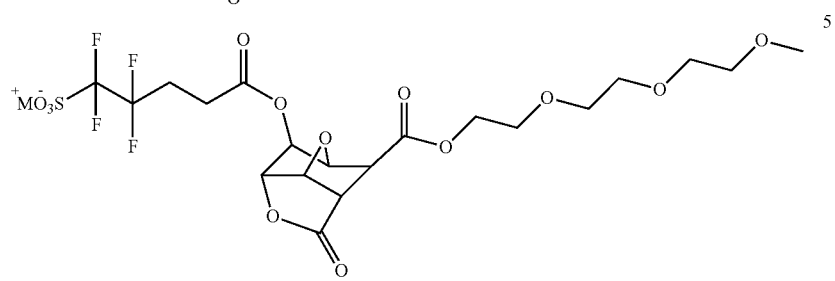
5
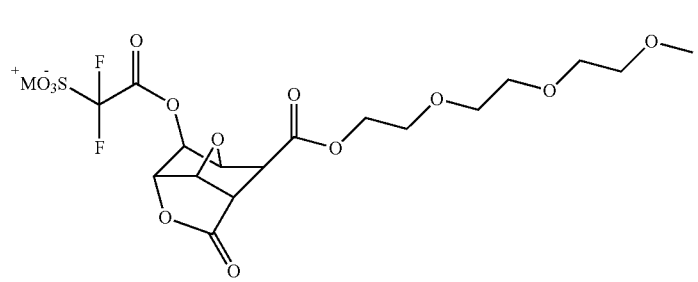
6
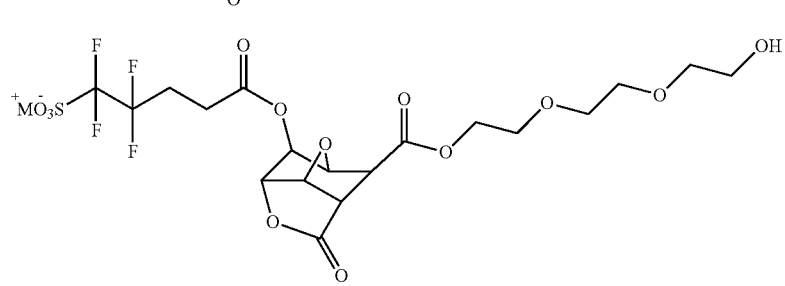
7
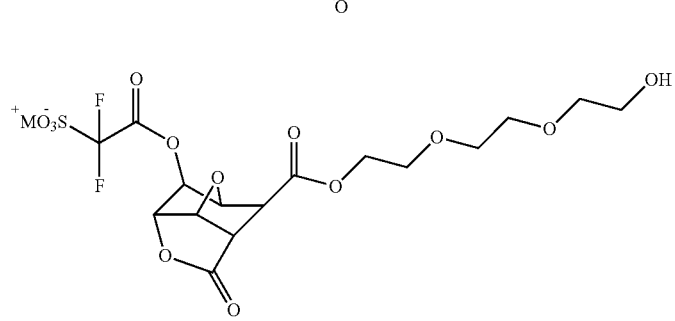
8

9
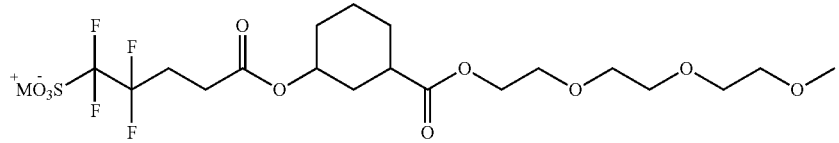
10
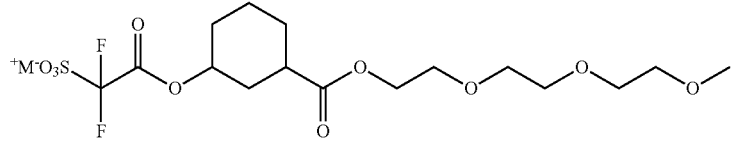
11
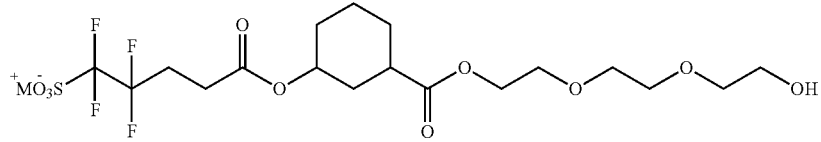
12
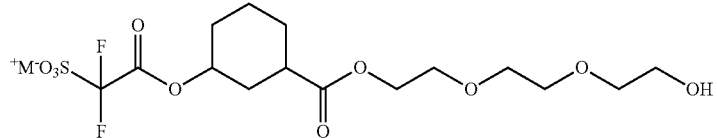
13
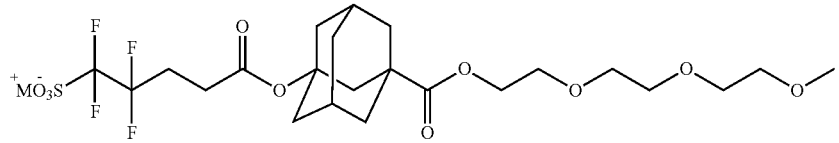
14
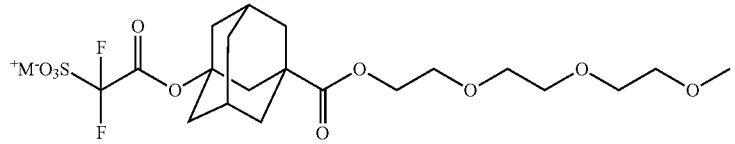
15
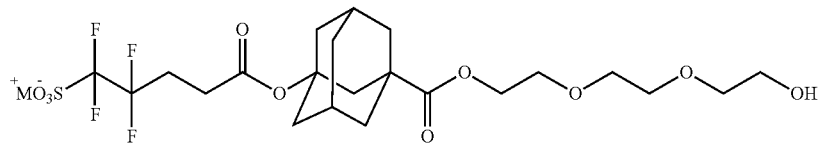
16
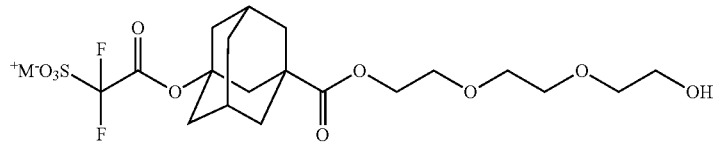
17
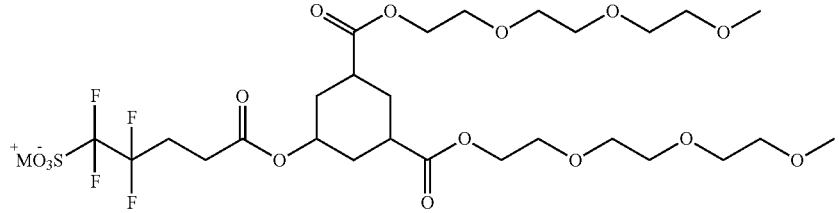

18
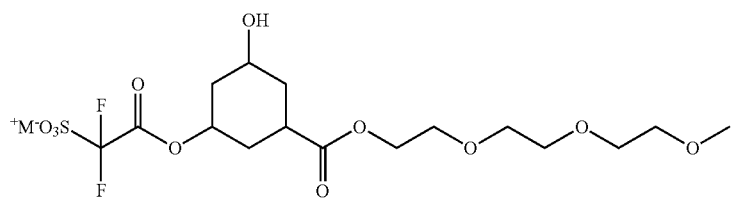
19
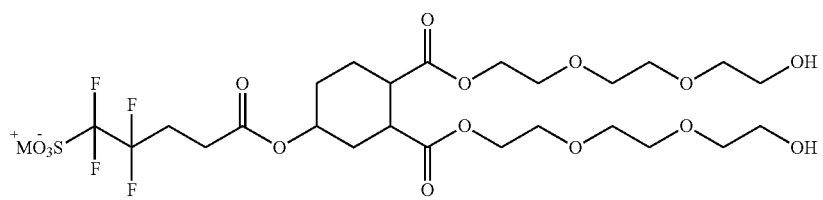
20
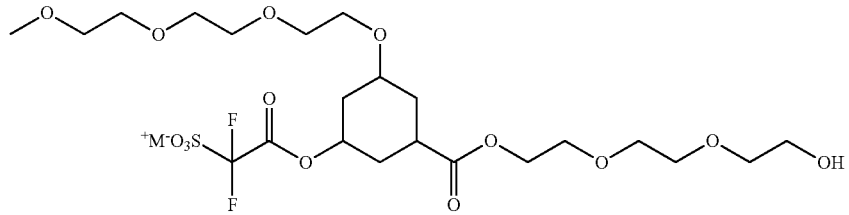
21
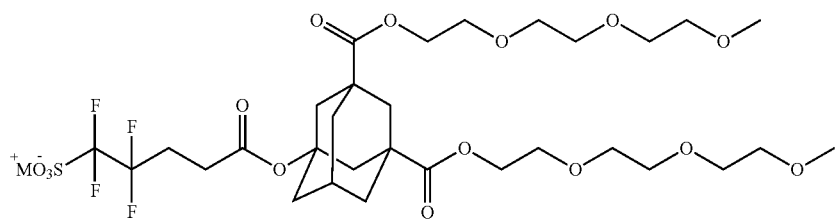
22
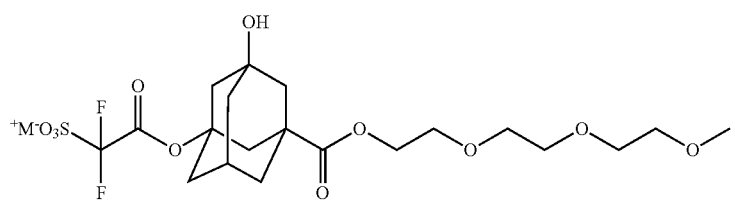
23
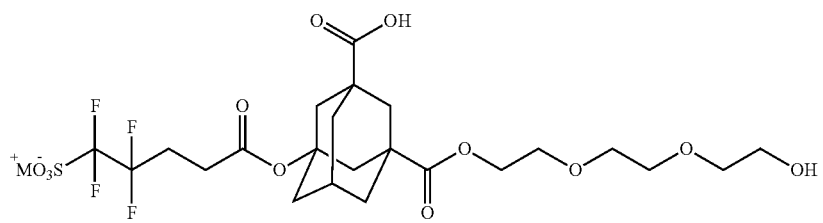
24
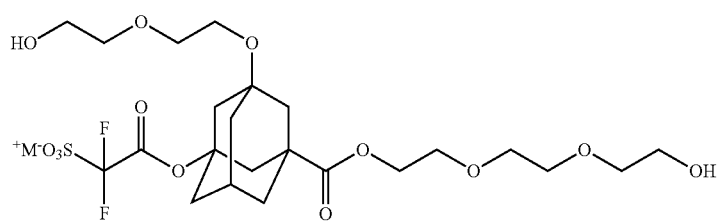
Acid generator compounds of the invention can be readily prepared. Exemplary preferred syntheses are set forth in the examples which follow. A preferred exemplary synthesis is also shown in the following Schemes 1-3:

Scheme 1:

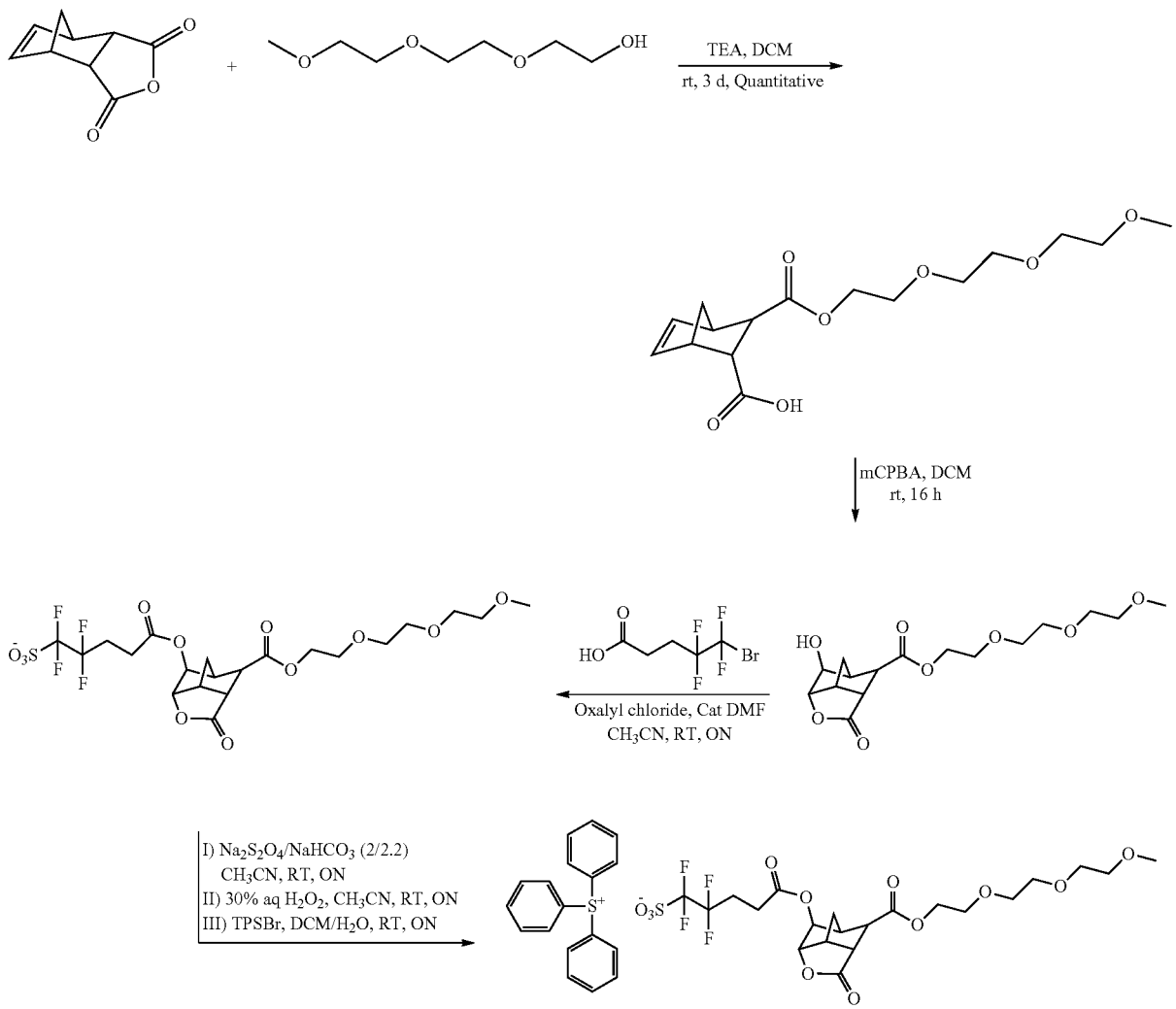

As generally depicted in the above Scheme 1, the reactive (unsaturated) anhydride is coupled with a nucleophilic hydrophilic reagent (in the Scheme 1, the hydroxyl alkoxy compound). In Scheme 1, that coupling ring-opens the anhydride. The compound then may be treated under oxidizing conditions, e.g. with a peroxy agent such as meta-chloroperoxybenzioc acid (mCPBA) followed by functionalization of the ring. In Scheme 1, a heteroalicyclic ring (lactone) is functionalized through oxidation of the ring unsaturation to provide the hydroxyl which reacts which the acid chloride reagent. A carboalicyclic ring could be functionalized in the same manner to provide the sulfonic acid precursor. That sulfonic acid precursor 4 shown in Scheme 1 above can then be sulfonated followed by coupling with the cation component to provide the desired acid generator compound.

Scheme 2:

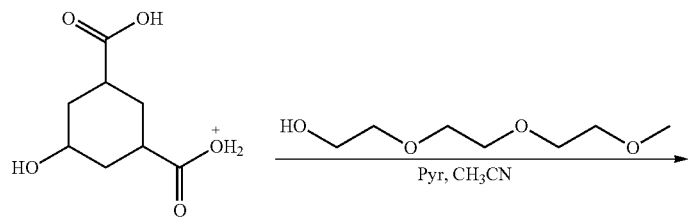

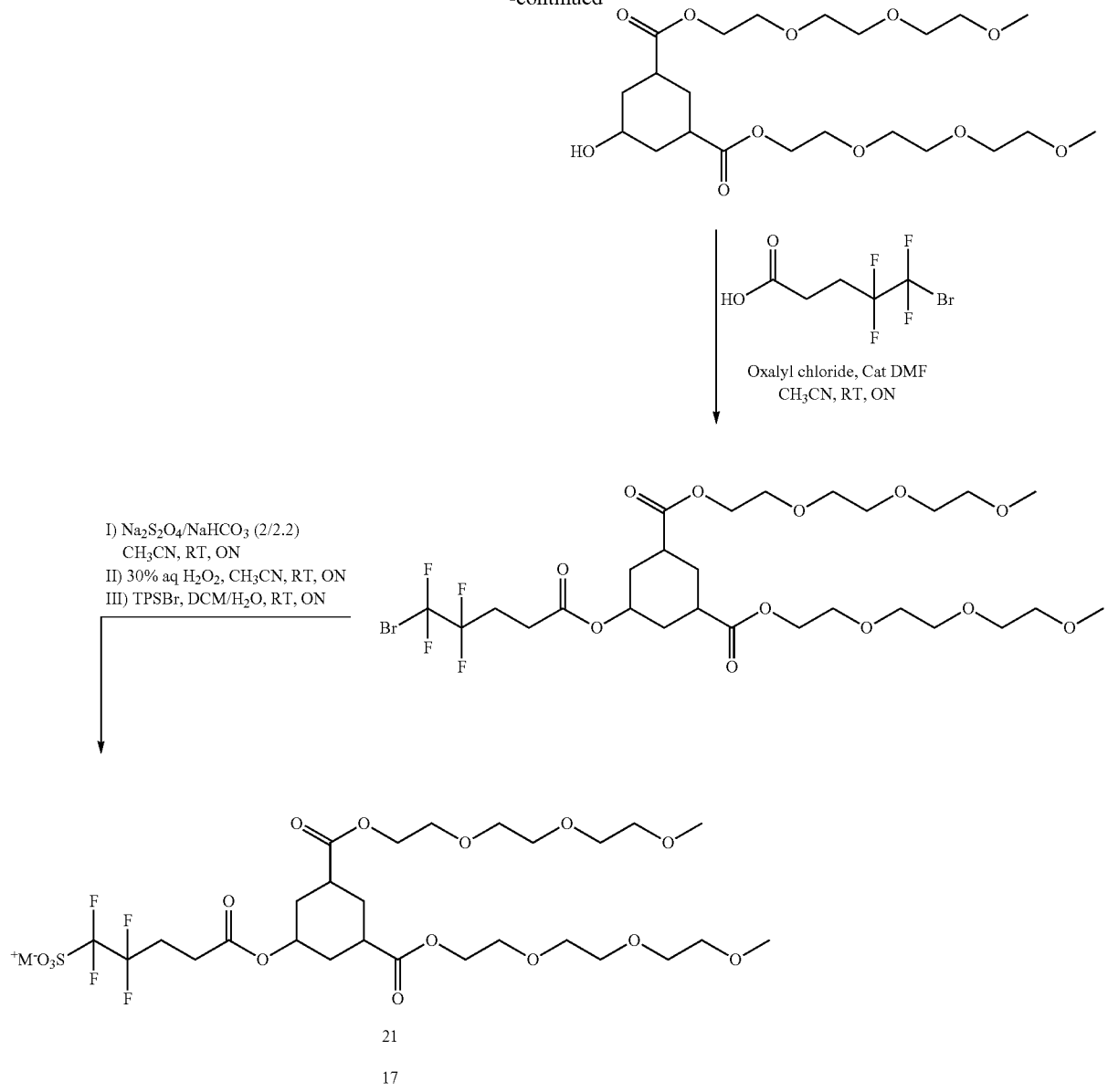

As generally depicted in the above Scheme 2, the substituted (reactive) cyclohexane is coupled with a nucleophilic hydrophilic reagent (in the Scheme 2, the hydroxyl alkoxy compound). In Scheme 2, that coupling occurs at carboxylic acid substitutes on the cyclohexane and thus forms ester bonds. In Scheme 2, the cyclohexane may be substituted with hydroxyl, and then the cyclohexane could be functionalized in the same manner to provide the sulfonic acid precursor. That sulfonic acid precursor 4 shown in Scheme 2 above can then be sulfonated followed by coupling with the cation component to provide the desired acid generator compound.

Scheme 3:

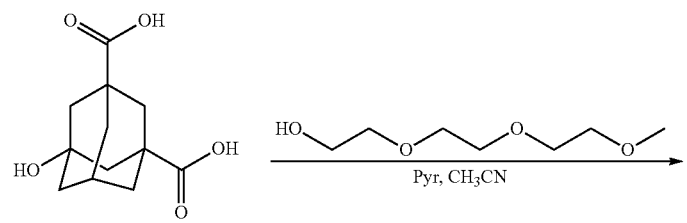

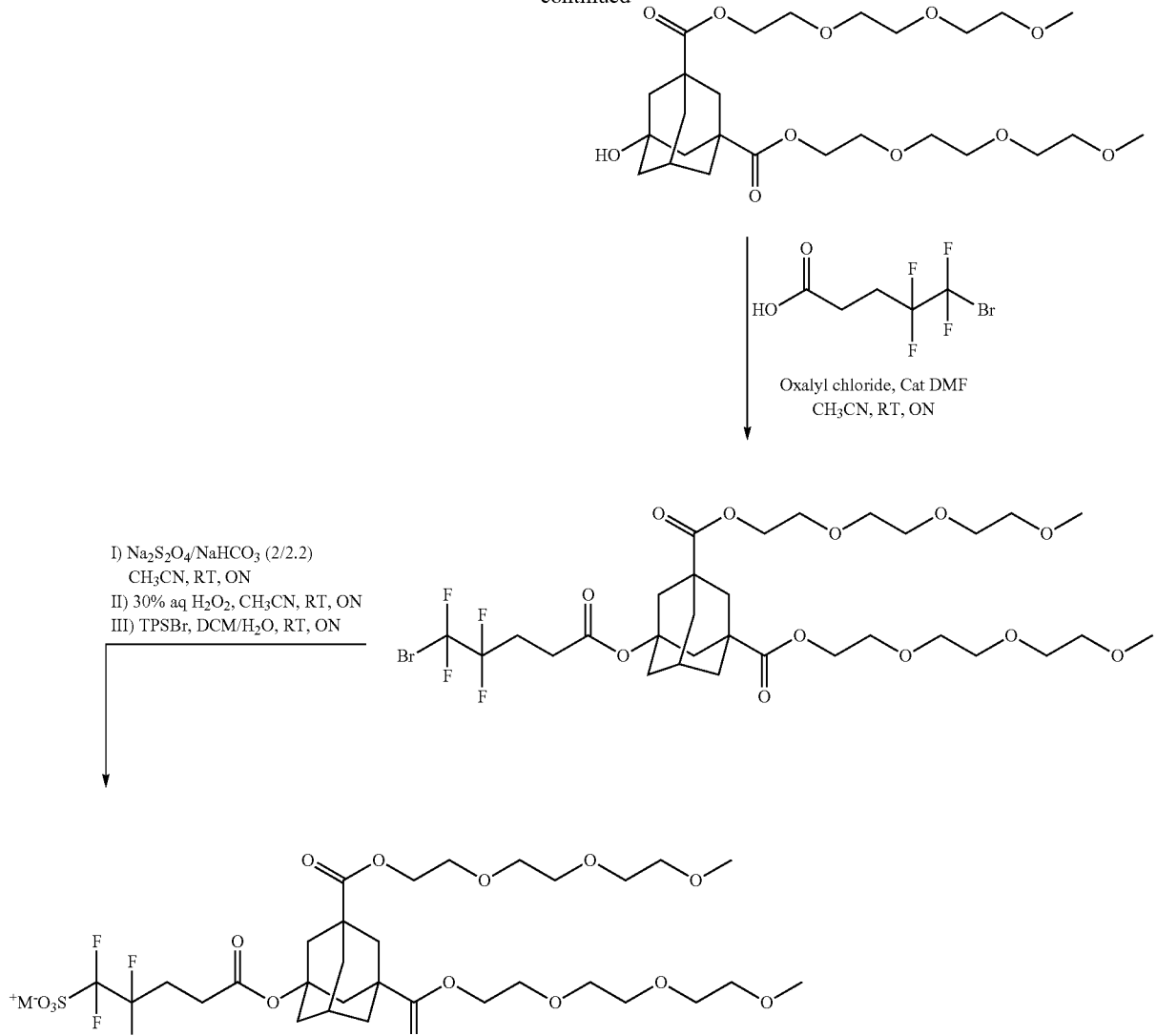

As generally depicted in the above Scheme 3, the substituted (reactive) polycycloalkane is coupled with a nucleophilic hydrophilic reagent (in the Scheme 3, the hydroxyl alkoxy compound). In Scheme 3, that coupling occurs at carboxylic acid substitutes on the polycycloalkane and thus forms ester bonds. In Scheme 3, the polycycloalkane may be substituted with hydroxyl, and then the polycycloalkane could be functionalized in the same manner to provide the sulfonic acid precursor. That sulfonic acid precursor 4 shown in Scheme 3 above can then be sulfonated followed by coupling with the cation component to provide the desired acid generator compound.

Photoresist Compositions

As discussed above, acid generator compounds as disclosed herein are useful as the radiation sensitive component in photoresist compositions, including both positive-acting and negative-acting chemically amplified resist compositions.

The photoresists of the invention typically comprise a polymer and one or more acid generator compounds as disclosed herein. Preferably the polymer has functional groups that impart alkaline aqueous developability to the resist composition. For example, preferred are polymers that comprise polar functional groups such as hydroxyl or carboxylate, or acid-labile groups that can liberate such polar moieties upon lithographic processing. Preferably the polymer is used in a resist composition in an amount sufficient to render the resist developable with an aqueous alkaline solution.

Acid generator compounds of the invention are also suitably used with polymers that comprise repeat units containing aromatic groups, such as optionally substituted phenyl including phenol, optionally substituted naphthyl, and optionally substituted anthracene. Optionally substituted phenyl (including phenol) containing polymers are particularly suitable for many resist systems, including those imaged with EUV and e-beam radiation. For positive-acting resists, the polymer also preferably contains one or more repeat units that comprise acid-labile groups. For example, in the case of polymers containing optionally substituted phenyl or other aromatic groups, a polymer may comprise repeat units that contain one or more acid-labile moieties such as a polymer that is formed by polymerization of monomers of an acrylate or methacrylate compound with acid-labile ester (e.g. t-butyl acrylate or t-butyl methacrylate). Such monomers may be copolymerized with one or more other monomers that comprise aromatic group(s) such as optionally phenyl, e.g. a styrene or vinyl phenol monomer.

Preferred monomers used for the formation of such polymers include: an acid-labile monomer having the below formula (V), a lactone-containing monomer of the formula (VI), a base-soluble monomer of formula (VII) for adjusting dissolution rate in alkaline developer, and a photoacid-generating monomer of the formula (VIII), or a combination comprising at least one of the foregoing monomers:

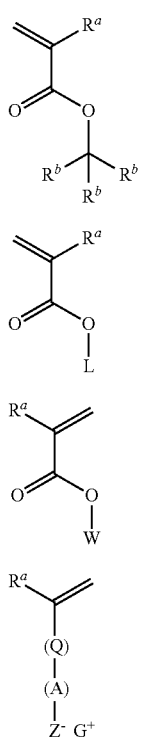

wherein each $R^a$ is independently H, F, —CN, $C_{1-10}$ alkyl, or $C_{1-10}$ fluoroalkyl. In the acid-deprotectable monomer of formula (V), $R^b$ is independently $C_{1-20}$ alkyl, $C_{3-20}$ cycloalkyl, $C_{6-20}$ aryl, or $C_{7-20}$ aralkyl, and each $R^b$ is separate or at least one $R^b$ is bonded to an adjacent $R^b$ to form a cyclic structure. In lactone-containing monomer of formula (VI), L is a monocyclic, polycyclic, or fused polycyclic $C_{4-20}$ lactone-containing group. In the base solubilizing monomer of formula (VII), W is a halogenated or non-halogenated, aromatic or non-aromatic $C_{2-50}$ hydroxyl-containing organic group having a pKa of less than or equal to 12. In the photoacid generating monomer of formula (VIII), Q is ester-containing or non-ester containing and fluorinated or non-fluorinated and is $C_{1-20}$ alkyl, $C_{3-20}$ cycloalkyl, $C_{6-20}$ aryl, or $C_{7-20}$ aralkyl group, A is ester-containing or non-ester-containing and fluorinated or non-fluorinated, and is $C_{1-20}$ alkyl, $C_{3-20}$ cycloalkyl, $C_{6-20}$ aryl, or $C_{7-20}$ aralkyl, $Z^-$ is an anionic moiety comprising carboxy-late, sulfonate, an anion of a sulfonamide, or an anion of a sulfonimide, and $G^+$ is a sulfonium or iodonium cation.

Exemplary acid-labile monomers include but are not limited to:

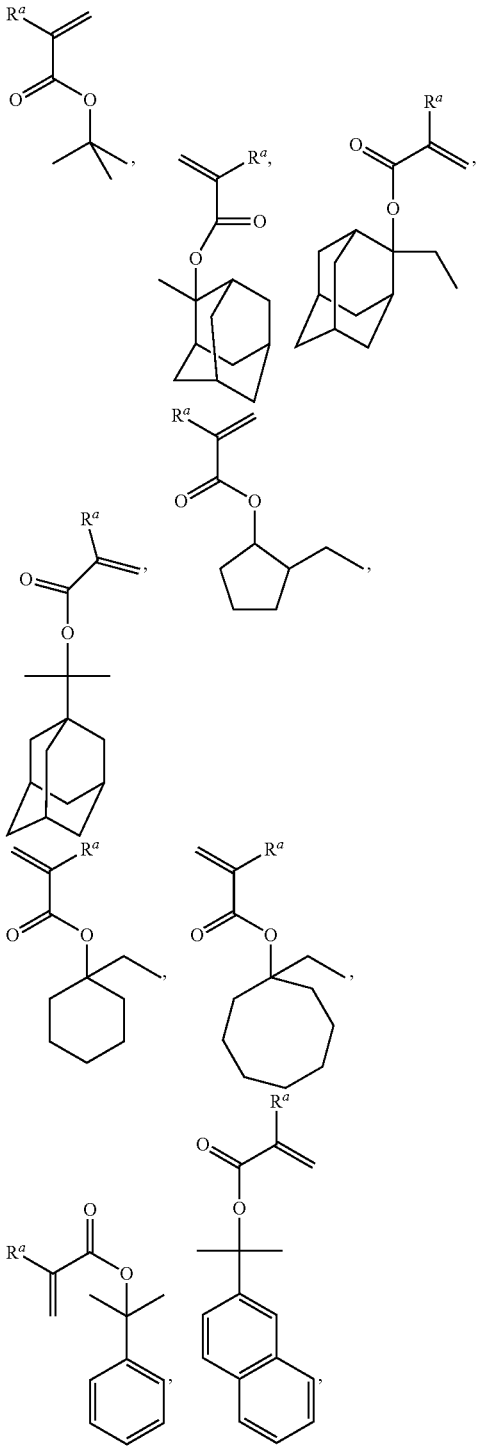

or a combination comprising at least one of the foregoing, wherein $R^a$ is H, F, —CN, $C_{1-6}$ alkyl, or $C_{1-6}$ fluoroalkyl.

Suitable lactone monomers may be of the following formula (IX):

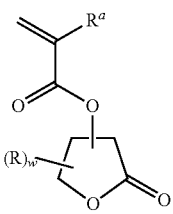

wherein $R^a$ is H, F, —CN, $C_{1-6}$ alkyl, or $C_{1-6}$ fluoroalkyl, R is a $C_{1-10}$ alkyl, cycloalkyl, or heterocycloalkyl, and w is an integer of 0 to 5. In formula (IX), R is attached directly to the lactone ring or commonly attached to the lactone ring and/or one or more R groups, and the ester moiety is attached to the lactone ring directly, or indirectly through R.

Exemplary lactone-containing monomers include:

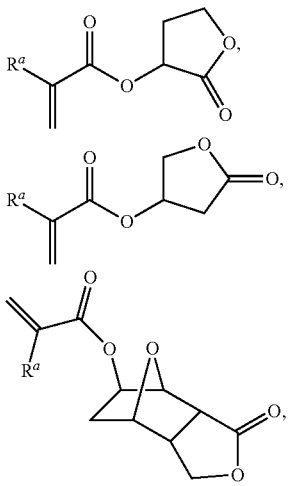

or a combination comprising at least one of the foregoing monomers, wherein $R^a$ is H, F, —CN, $C_{1-10}$ alkyl, or $C_{1-10}$ fluoroalkyl.

Suitable base-soluble monomers may be of the following formula (X):

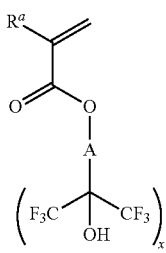

wherein each $R^a$ is independently H, F, —CN, $C_{1-10}$ alkyl, or $C_{1-10}$ fluoroalkyl, A is a hydroxyl-containing or non-hydroxyl containing, ester-containing or non ester-containing, fluorinated or non fluorinated $C_{1-20}$ arylene, or $C_{7-20}$ aralkylene, and x alkylene, $C_{3-20}$ cycloalkylene, $C_{6-20}$ is an integer of from 0 to 4, wherein when x is 0, A is a hydroxyl-containing $C_{6-20}$ arylene.

Exemplary base soluble monomers include those having the following structures:

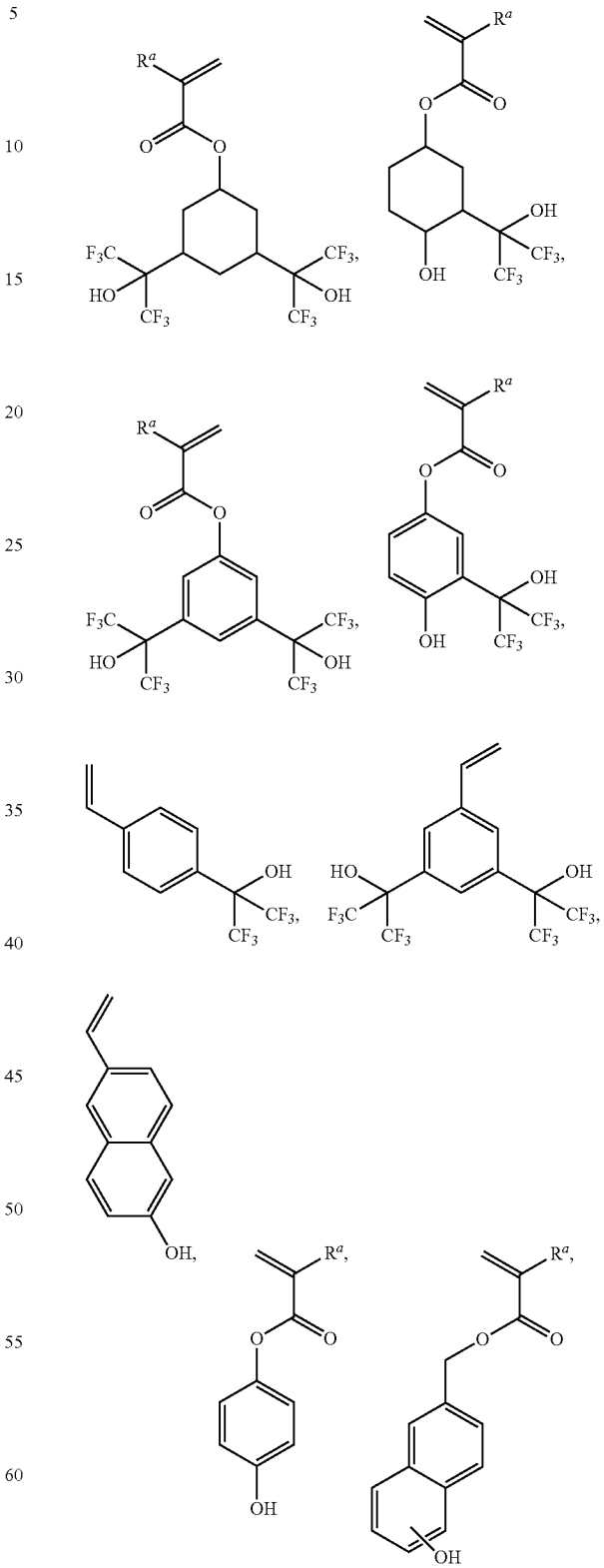

or a combination comprising at least one of the foregoing, wherein $R^a$ is H, F, —CN, $C_{1-6}$ alkyl, or $C_{1-6}$ fluoroalkyl.

Preferred photoacid generating monomer include those of the formulae (XI) or (XII):

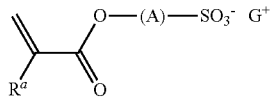
(XI)

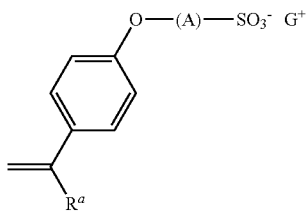
(XII)

wherein each $R^a$ is independently H, F, —CN, $C_{1-6}$ alkyl, or $C_{1-6}$ fluoroalkyl, A is a fluorine-substituted $C_{1-30}$ alkylene group, a fluorine-substituted $C_{3-30}$ cycloalkylene group, a fluorine-substituted $C_{6-30}$ arylene group, or a fluorine-substituted $C_{7-30}$ alkylene-arylene group, and $G^+$ is a sulfonium or iodonium cation.

Preferably, in formulas (XI) and (XII), A is a —[C(R$^1$)$_2$)$_x$C(=O)O]$_b$—C((R$^2$)$_2$)$_y$(CF$_2$)$_z$— group, or an o-, m- or p-substituted —C$_6$F$_4$— group, where each $R^1$ and $R^2$ are each independently H, F, —CN, $C_{1-6}$ fluoroalkyl, or $C_{1-6}$ alkyl, b is 0 or 1, x is an integer of 1 to 10, y and z are independently integers of from 0 to 10, and the sum of y+z is at least 1.

Exemplary preferred photoacid generating monomers include:

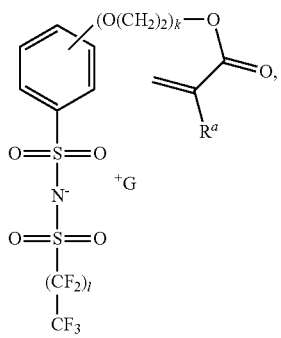

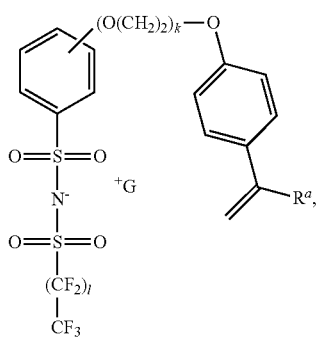

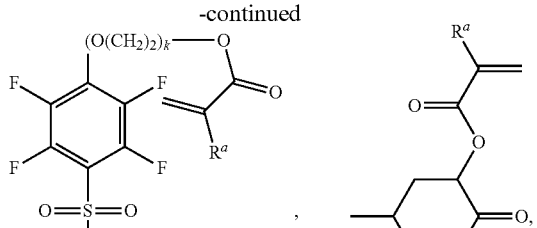

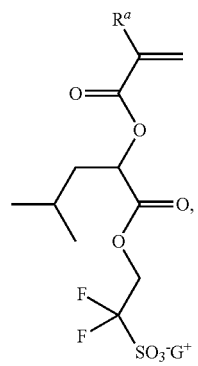

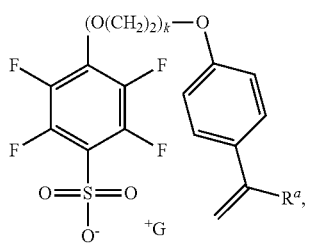

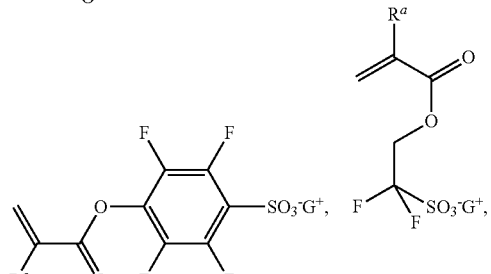

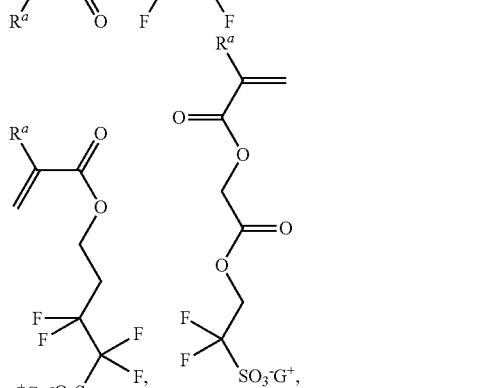

or a combination comprising at least one of the foregoing, where each $R^a$ is independently H, F, —CN, $C_{1-6}$ alkyl, or $C_{1-6}$ fluoroalkyl, k is suitably an integer of from 0 to 5; and $G^+$ is a sulfonium or iodonium cation.

Preferred photoacid-generating monomers may include sulfonium or iodonium cation. Preferably, in formula (IV), $G^+$ is of the formula (XIII):

(XIII)

wherein X is S or I, each $R^0$ is halogenated or non-halogenated and is independently $C_{1-30}$ alkyl group; a polycyclic or monocyclic $C_{3-30}$ cycloalkyl group; a polycyclic or monocyclic $C_{4-30}$ aryl group; or a combination comprising at least one of the foregoing, wherein when X is S, one of the $R^0$ groups is optionally attached to one adjacent $R^0$ group by a single bond, and a is 2 or 3, wherein when X is I, a is 2, or when X is S, a is 3.

Exemplary acid generating monomers include those having the formulas:

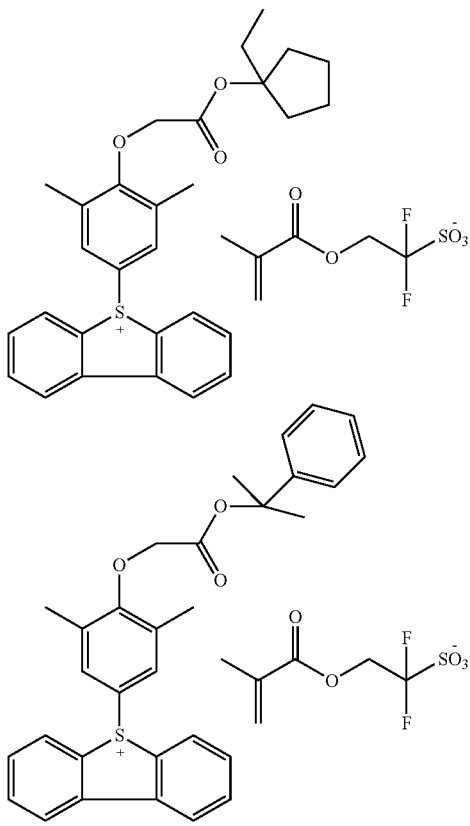

wherein $R^a$ is H, F, —CN, $C_{1-6}$ alkyl, or $C_{1-6}$ fluoroalkyl.

Specifically suitable polymers that have acid-labile deblocking groups for use in a positive-acting chemically-amplified photoresist of the invention have been disclosed in European Patent Application 0829766A2 (polymers with acetal and ketal polymers) and European Patent Application EP0783136A2 (terpolymers and other copolymers including units of 1) styrene; 2) hydroxystyrene; and 3) acid labile groups, particularly alkyl acrylate acid labile groups.

Polymers for use in photoresists of the invention may suitably vary widely in molecular weight and polydispersity. Suitable polymers include those that have a $M_w$ of from about 1,000 to about 50,000, more typically about 2,000 to about 30,000 with a molecular weight distribution of about 3 or less, more typically a molecular weight distribution of about 2 or less.

Preferred negative-acting compositions of the invention comprise a mixture of materials that will cure, crosslink or harden upon exposure to acid, and a photoactive component of the invention. Preferred negative acting compositions comprise a polymer binder such as a phenolic or non-aromatic polymer, a crosslinker component and one or more acid generators of the invention. Such compositions and the use thereof have been disclosed in European Patent Applications 0164248 and U.S. Pat. No. 5,128,232 to Thackeray et al. Preferred phenolic polymers for use as the polymer binder component include novolaks and poly(vinylphenol)s such as those discussed above. Preferred crosslinkers include amine-based materials, including melamine, glycolurils, benzoguanamine-based materials and urea-based materials. Melamine-formaldehyde polymers are often particularly suitable. Such crosslinkers are commercially available, e.g. the melamine polymers, glycoluril polymers, urea-based polymer and benzoguanamine polymers, such as those sold by Cytec under tradenames Cymel 301, 303, 1170, 1171, 1172, 1123 and 1125 and Beetle 60, 65 and 80.

Photoresists of the invention also may contain other materials. For example, other optional additives include actinic and contrast dyes, anti-striation agents, plasticizers, speed enhancers, sensitizers, photodestroyable bases etc. Such optional additives typically will be present in minor concentration in a photoresist composition.

Inclusion of base materials, preferably the carboxylate or sulfonate salts of photo-decomposable cations, provides a mechanism for neutralization of acid from the acid decomposable groups, and limits the diffusion of the photogenerated acid, to thereby provide improved contrast in the photoresist.

Photo-destroyable bases include photo-decomposable cations, and preferably those also useful for preparing acid generator compounds, paired with an anion of a weak (pKa >2) acid such as, for example, a $C_{1-20}$ carboxylic acid. Exemplary such carboxylic acids include formic acid, acetic acid, propionic acid, tartaric acid, succinic acid, cyclohexylcarboxylic acid, benzoic acid, salicylic acid, and other such carboxylic acids.

Alternatively, or in addition, other additives may include quenchers that are non-photo-destroyable bases, such as, for example, those based on hydroxides, carboxylates, amines, imines, and amides. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as tripropylamine, dodecylamine, 1,1',1''-nitrilotripropan-2-ol, 1,1',1'',1'''-(ethane-1,2-diylbis(azanetriyl))tetrapropan-2-ol; aryl amines such as diphenylamine, triphenylamine, aminophenol, and 2-(4-aminophenyl)-2-(4-hydroxyphenyl)propane, Troger's base, a hindered amine such as diazabicycloundecene (DBU) or diazabicyclononene (DBN), or ionic quenchers including quaternary alkyl ammonium salts such as tetrabutylammonium hydroxide (TBAH) or tetrabutylammonium lactate.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoresist further includes a solvent generally suitable for dissolving, dispensing, and coating the components used in a photoresists. Exemplary solvents include anisole, alcohols including ethyl lactate, 1-methoxy-2-propanol, and 1-ethoxy-2 propanol, esters including n-butylacetate, 1-methoxy-2-propyl acetate, methoxyethoxypropionate, ethoxyethoxypropionate, ketones including cyclohexanone and 2-heptanone, and a combination comprising at least one of the foregoing solvents.

Such photoresists may include the copolymer in an amount of 50 to 99 wt %, specifically 55 to 95 wt %, more specifically 60 to 90 wt %, and still more specifically 65 to 90 based on the total weight of solids. The photo-destroyable base may be present in the photoresist in an amount of 0.01 to 5 wt %, specifically 0.1 to 4 wt %, and still more specifically 0.2 to 3 wt %, based on the total weight of solids. A surfactant may be included in an amount of 0.01 to 5 wt %, specifically 0.1 to 4 wt %, and still more specifically 0.2 to 3 wt %, based on the total weight of solids. A quencher may be included in relatively small amounts of for example, from 0.03 to 5 wt % based on the total weight of solids. Other additives may be included in amounts of less than or equal to 30 wt %, specifically less than or equal to 20%, or more specifically less than or equal to 10%, based on the total weight of solids. The total solids content for the photoresist composition may be 0.5 to 50 wt %, specifically 1 to 45 wt %, more specifically 2 to 40 wt %, and still more specifically 5 to 30 wt %, based on the total weight of solids and solvent. The acid generator compound(s) should be present in an amount sufficient to enable generation of a latent image in a coating layer of the resist. More specifically, the one or more acid generator compounds will suitably be present in an amount of from about 1 to 50 weight percent of total solids of a resist. It will be understood that the solids includes copolymer, photo-destroyable base, quencher, surfactant, any added PAG, and any optional additives, exclusive of solvent.

A coated substrate may be formed from the photoresist containing acid generator compound(s) which should be present in an amount sufficient to enable generation of a latent image in a coating layer of the resist and acid generator compound. Such a coated substrate includes: (a) a substrate having one or more layers to be patterned on a surface thereof; and (b) a layer of the photoresist composition including the acid generator compound over the one or more layers to be patterned. For EUV or e beam imaging, photoresists may suitably have relatively higher content of acid generator compound(s), e.g. where the one or more acid generator compounds comprise 5 to 10 to about 65 weight percent of total solids of the resist. Typically, lesser amounts of the photoactive component will be suitable for chemically amplified resists.

The photoresists of the invention are generally prepared following known procedures with the exception that one or more acid generator compounds of the invention are substituted for prior photoactive compounds used in the formulation of such photoresists. The photoresists of the invention can be used in accordance with known procedures.

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOL strained silicon, and other such substrate materials, formed as circular wafers having dimensions such as, for example, 20 cm, 30 cm, or larger in diameter, or other dimensions useful for wafer fabrication production.

Further, a method of forming an electronic device includes (a) applying a layer of a photoresist composition including on a surface of the substrate; (b) patternwise exposing the photoresist composition layer to activating radiation; and (c) developing the exposed photoresist composition layer to provide a resist relief image.

Applying may be accomplished by any suitable method, including spin coating, spray coating, dip coating, doctor blading, or the like. Applying the layer of photoresist is preferably accomplished by spin-coating the photoresist in solvent using a coating track, in which the photoresist is dispensed on a spinning wafer. During dispense, the wafer may be spun at a speed of up to 4,000 rpm, preferably from about 500 to 3,000 rpm, and more preferably 1,000 to 2,500 rpm. The coated wafer is spun to remove solvent, and baked on a hot plate to remove residual solvent and free volume from the film to make it uniformly dense.

Patternwise exposure is then carried out using an exposure tool such as a stepper, in which the film is irradiated through a pattern mask and thereby is exposed pattern-wise. The method preferably uses advanced exposure tools generating activating radiation at wavelengths capable of high resolution including extreme-ultraviolet (EUV) or e-beam radiation. It will be appreciated that exposure using the activating radiation decomposes the PAG in the exposed areas and generates acid and decomposition by-products, and that the acid then effects a chemical change in the polymer (deblocking the acid sensitive group to generate a base-soluble group, or alternatively, catalyzing a cross-linking reaction in the exposed areas). The resolution of such exposure tools may be less than 30 nm.

Developing the exposed photoresist layer is then accomplished by treating the exposed layer to a suitable developer capable of selectively removing the exposed portions of the film (where the photoresist is positive tone) or removing the unexposed portions of the film (where the photoresist is crosslinkable in the exposed regions, i.e., negative tone). Preferably, the photoresist is positive tone based on a polymer having acid sensitive (deprotectable) groups, and the developer is preferably a metal-ion free tetraalkylammonium hydroxide solution, such as, for example, aqueous 0.26 N tetramethylammonium hydroxide. A pattern forms by developing.

Additionally, for positive resists, unexposed regions can be selectively removed by treatment with a suitable nonpolar solvent for negative tone development. See U.S. 2011/0294069 for suitable procedures for negative tone development of positive photoresists. Typical nonpolar solvents for negative tone development are organic developers, such as a solvent chosen from ketones, esters, hydrocarbons, and mixtures thereof, e.g. acetone, 2-hexanone, methyl acetate, butyl acetate, and terahydrofuran.

The photoresist may, when used in one or more such a pattern-forming processes, be used to fabricate electronic and optoelectronic devices such as memory devices, processor chips (CPU's), graphics chips, and other such devices.

The following examples are illustrative of the invention.

Example 1: Synthesis of PAG-A1

The PAG-A1 was prepared as outlined in the following Scheme A:

Scheme A:

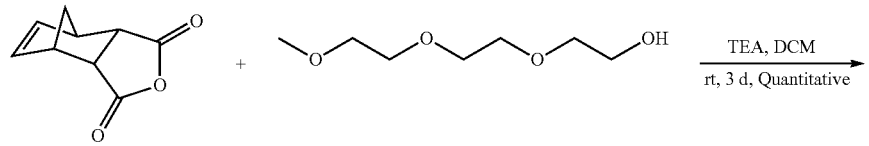

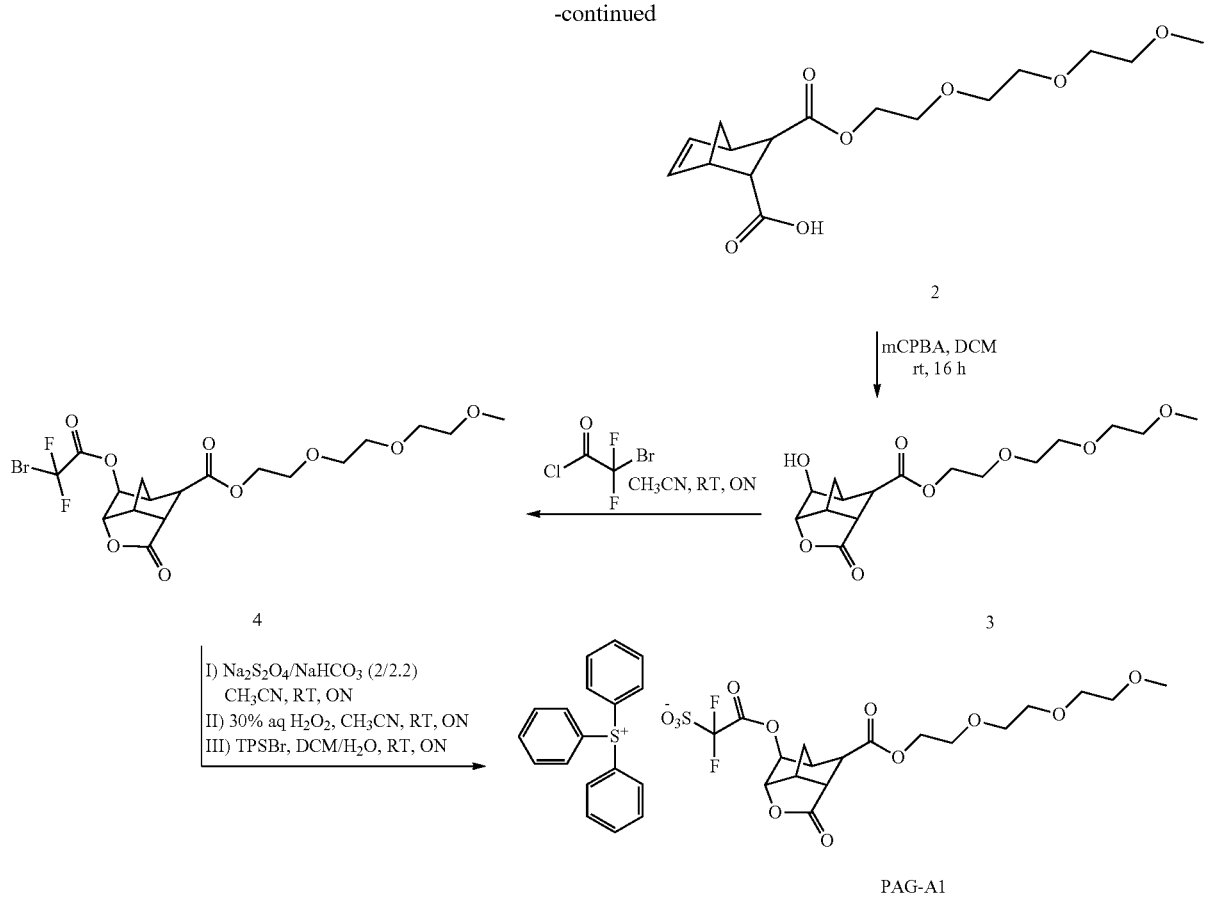

PAG-A1

To a mixture of cis-5-norbornen-endo-2,3-dicarboxylic anhydride (1, 16 g, 97.5 mmol) and 2-(2-(2-methoxyethoxy)ethoxy)ethanol (16 g, 97.5 mmol) in dichloromethane (250 mL) at room temp was added slowly triethylamine (14.8 g, 146.2 mmol). The reaction mixture was stirred at room temperature for 3 days. Upon completion of reaction, the mixture was acidified with 6N HCl (150 mL). The organic layer was separated, dried and conc. to get the product (2) in 90% yield (28.8 g) which was used as such without any further purification. $^1$H NMR ((CD$_3$)$_2$CO, 300 MHz): δ 1.35 (m, 2H), 2.03 (m, 1H), 3.08 (s, 2H), 3.27 (s, 3H), 3.31 (m, 2H), 3.46 (m, 2H), 3.56 (m, 8H), 4.03 (m, 2H), 6.08 (m, 1H), 6.18 (m, 1H). To a solution of compound (2) (15.43 g, 47 mmol) in dichloromethane (200 mL) was added as meta-chloroperoxybenzioc acid (mCPBA) (17.3 g, 100 mmol). The reaction mixture was stirred at room temperature for 16 h. After the reaction completion, ethyl acetate (50 mL) and water (5 mL) was added to the mixture. The organic layer was separated, washed with dilute NaHCO$_3$ followed by water (50 mL). The organic layer was evaporated to provide white solids. Redissolved the white solids in dichloromethane and passed through silica plug eluting with dichloromethane. The organic part was evaporated to yield the product (3) in 89% yield (14 g). $^1$H NMR (CDCl$_3$, 300 MHz): δ 1.61 (d, 1H), 2.20 (d, 1H), 2.77 (m, 2H), 3.06 (m, 1H), 3.26 (t, 1H), 3.39 (s, 3H), 3.57 (m, 2H), 3.64 (m, 9H), 4.18 (m, 1H), 4.3 (s, 1H), 4.42 (m, 1H), 4.5 (d, 1H). To the solution of compound (3) (20 g, 60 mmol) in acetonitrile (100 mL) was added pyridine (5.24 g, 66 mmol) followed by slow addition of 2-bromo-2,2-difluoroacetyl chloride (11.82 g, 61 mmol). The resulting reaction mixture was stirred overnight at room temp. Upon completion of reaction, solvent was evaporated, the residue was redissolved in dichloromethane (300 mL), washed with 1N HCl (100 mL) followed by Millipore deionized water (100 ml). The organic part was evaporated to yield crude product (4) in 85% yield (25 g) which was used as such without further purification. $^1$H NMR (CDCl$_3$, 300 MHz): δ 1.39 (d, 1H), 1.72 (d, 1H), 2.53 (m, 2H), 2.79 (m, 1H), 3.0 (m, 4H), 3.26 (m, 2H), 3.28 (m, 8H), 3.94 (m, 2H), 4.31 (d, 1H), 5.14 (s, 1H). $^{19}$F NMR: δ −61.77.

To a solution of compound (7) (25 g, 50 mmol) in acetonitrile (250 mL) was added solution of sodium dithionite (13 g, 74.6 mmol) and sodium hydrogen carbonate (7 g, 83.3 mmol) in 200 mL of water. The mixture was stirred at room temp for 18 h. Upon completion the solvents were fully removed under reduced pressure. The resulting residue was dried under vacuum. The residue was suspended in 300 mL of dichloromethane and the suspension was stirred for 2 h. The undissolved salts were filtered off and to the resulting dichloromethane solution was added 11 g of 30% aqueous solution of hydrogen peroxide. The mixture was stirred at room temperature for 16 h. $^{19}$F NMR showed complete conversion. A 50 mL aqueous solution sodium disulfite (5 M) was added to neutralize excess of hydrogen peroxide. The solvents were fully removed under reduced pressure. The crude residue was redissolved in dichloromethane, dried over MgSO$_4$, filtered and the solvent was removed under reduced pressure to produce 25 g of crude sulfonate which was used in the next step without further purification.

Triphenylsulfonium bromide (TPSBr) (17 g, 49 mmol) and crude sulfonate from previous step (25 g, 48 mmol) were dissolved in 250 mL dichloromethane and 40 mL deionized water, and stirred at room temperature for 16 hours under nitrogen. Upon completion, the organic phase of the resulting biphasic mixture was separated. The organic phase was gravity filtered through filter paper to remove traces of water. The solvent was then removed by rotary evaporation to yield crude product (PAG-A1) which was purified by silica gel column chromatography eluting with dichloromethane to yield PAG-A1 in 70% yield (25 g). $^1$H NMR (CDCl$_3$, 300 MHz): δ 1.66 (d, 1H), 2.38 (d, 1H), 2.82 (m, 1H), 3.13 (m, 1H), 3.2 (s, 1H), 3.28 (t, 1H), 3.36 (s, 3H), 3.55 (m, 2H), 3.65 (m, 8H), 4.25 (m, 2H), 4.76 (d, 1H), 5.4 (s, 1H), 7.71 (bs, 15H). $^{19}$F NMR: δ −110.68.

Example 2: Acid Diffusion Measurement

Acid diffusion measurements were determined by the following procedure. An acid detector layer formulation was prepared by combining an acid cleavable polymer A1 (2-adamantyl-2-propyl methacrylate/alpha-(gammabutyrolactone) methacrylate/1-hydroxyadamantyl-3-methacrylate terpolymers, 30/50/20 molar ratio, Mw=10K g/mol), shown below (5.981 wt % of total formulation):

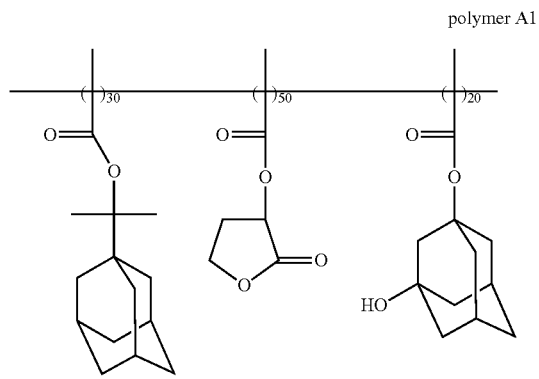

polymer A1 and tert-butyl 4-hydroxypiperdine-1-carboxylate as a quencher (0.019 wt % of total formulation) in a 50/50 (w/w) mixture of propylene glycol methyl ether acetate (PGMEA) and methyl 2-hydroxyisobutyrate (HBM). Separately, an acid source layer formulation was prepared by combining a t-butylacrylate/methacrylic acid 70/30 mole percent, for 100 mol percent of monomers) copolymer (0.891% of solution) and the PAG (153.40 μmol/g based on the total formulation) in an 80/20 (w/w) mixture of 2-methyl-1-butanol and decane. The acid detector layer formulation and acid source layer solutions were each filtered separately using a 0.2 μm polytetrafluoroethylene (PTFE) syringe filter.

The substrate (Si wafer, 200 mm) was coated with a AR77 antireflective coating (available Rohm & Haas) and baked at 205° C. for 60 seconds to form an antireflective layer of 84 nm thickness, and 120 nm of the acid detector layer formulation was coated on the antireflective layer with baking at 110° C. for 60 seconds. The acid source layer formulation was then coated on the acid detector layer and baked at 90° C. for 60 seconds. All coating processes were carried out on a TEL ACT 8 coating track manufactured by Tokyo Electron.

The wafer so coated was then open frame exposed over 100 dose increments (separate doses) starting from an initial dose of 1 mJ/cm$^2$ at increments of 0.2 mJ/cm$^2$ using a 193 exposure tool (/1100 Stepper manufactured by ASML) and annular illumination. The wafer was post exposure baked (PEB) at 110° C. for 60 seconds or 120° C. for 60 seconds. During the PEB step the acid released during exposure in the acid source layer diffused into the acid detector layer causing deprotection of the acid labile group of the polymer of the acid detector layer After PEB, the pattern was developed using 0.26N aqueous tetramethylammonium hydroxide (TMAH) solution. The film thickness difference between the unexposed regions and exposed regions of the pattern is the total film loss (ΔL). The greater the film thickness loss in the exposed region, the greater the acid diffusion.

The diffusivity of the PAG, D, is defined by Fick's law of diffusion (equation 1):

$$D=(\Delta L/2 * erfc\, E_{th}/E)2/t_{PEB} \qquad \text{(equation 1)}$$

where ΔL is the difference in thickness between the exposed and unexposed areas (also referred to herein as the film thickness loss), $t_{PEB}$ is the PEB time, erfc is the error function complement, $E_{th}$ is the exposure dose (in mJ/cm$^2$) at which film thickness loss was observed for the first time, and E is the exposure dose (in mJ/cm$^2$). Once the diffusivity was determined, the diffusion length, DL, was then calculated using equation 2:

$$DL=2*(D*t_{PEB})^{1/2} \qquad \text{(equation 2)}$$

The diffusion length data for the exemplary and comparative PAGS are summarized in Table 1, below.

TABLE 1

| | | | PAG acid diffusion length (nm) at PEB = 100° C./60 sec | PAG acid diffusion length (nm) at PEB = 120° C./60 sec |
|---|---|---|---|---|
| Example | PAG | Anion Structure | | |
| Comparative PAG 1 | Triphenylsulfonium perfluotobutanesulfonate | F F F F F F F F C-C-C-C-SO$_3^-$ | 45.1 | 88.3 |

TABLE 1-continued

Results of PAGs acid diffusion length

| Example | PAG | Anion Structure | PAG acid diffusion length (nm) at PEB = 100° C./60 sec | PAG acid diffusion length (nm) at PEB = 120° C./60 sec |
|---|---|---|---|---|
| Comparative PAG 2 | Triphenylsulfonium 13,13-difluoro-12-oxo-2,5,8,11-tetraoxa-tridecane-13-sulfonate | | 30.4 | 61.4 |
| PAG-A1 | PAG-A1 | | 17.4 | 36.4 |

To ensure equal photoacid generation quantum yield, all PAGs were loaded at equal molar ratio. The hydrophilic PAG-A1 was compared to the comparative PAGs TPS PFBuS, TPS MTEG CDFMS. As can be seen in Table 1, and expected, PAG-A1 is much slower diffusing PAG than both comparative PAGs due to bulky anion unit. Similar acid diffusion trend was noticed at both PEB temperatures of 110° C. and at 120° C. As can be seen in Table 1, the acid diffusion measurements indicate a slower acid diffusion length for PAG-A1 at PEB temperatures of 110 and 120° C. when compared with the linear PAGs (TPS PFBuS and TPS MTEG CDFMS). These results show that the present PAGs can be incorporated into a photoresist composition to provide well resolved resist images.

Example 3: Lithographic Evaluation

The acid generators were evaluated lithographically according to the following procedure. Photoresists were formulated using the components and proportions shown in Table 2. The commercial photoresist polymer A2 was used in all examples. Polymer A2 is a pentapolymer incorporating monomers M1, M2, M3, M4 and M5 (structures of M1, M2, M3, M4 and M5 shown below), where the mole percentage of M1/M2/M3/M4/M5 is 20/20/30/20/10 for a total of 100 mole percent of monomers. The weight average molecule weight of the polymer was about 8,000 g/mol. Note that the PAG (see Table 2), base (t-butyloxycarbonyl-4-hydroxy-pyridine, TBOC-4HP), and surface leveling agent (surfactant) PF 656, available from Omnova, are in weight percent based on 100% solids content, with the balance of the solids being the polymer. The solvents used in these formulations are PGMEA (S1) and HBM (S2). The final % solids in both examples were 4 wt %. The weight ratio of solvent S1:S2 in the final formulation was 1:1. Structures of the comparative PAGs are shown in Table 2 below.

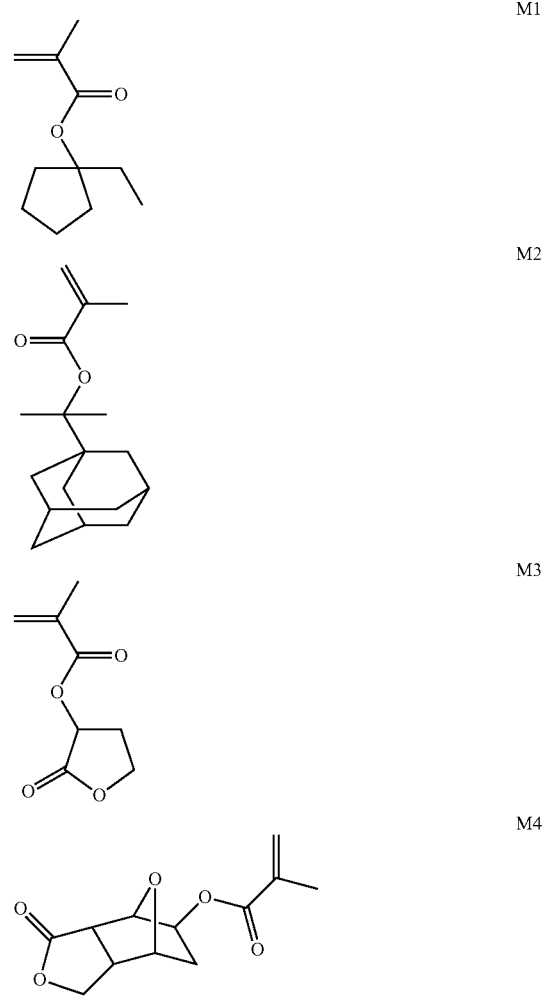

-continued

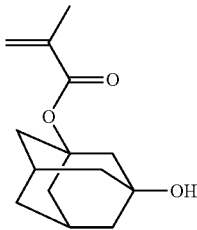
M5 seconds followed by developing with 0.26 N aqueous tetramethylammonium hydroxide (TMAH) developer and subsequent water wash.

In each example, a L/S pattern having a line width of 90 nm and a pitch of 180 nm was formed. Mask Error Factor (MEF) and Exposure Latitude (EL) and LWR (Line Width Roughness) were determined by processing the image captured by top-down scanning electron microscopy (SEM) using a Hitachi 9380 CD-SEM, operating at an accelerating voltage of 800 volts (V), probe current of 8.0 picoamperes (pA), using 200 K× magnification. Exposure latitude (EL) was defined as a difference in exposure energy to print

TABLE 2

| PAG | PAG Name | Structure of the PAG |
|---|---|---|
| Comparative PAG 1 | Triphenylsulfonium perfluorobutane-sulfonate | |
| Comparative PAG 2 | Triphenylsulfonium 13,13-difluoro-12-oxo-2,5,8,11-tetraoxatridecane-13-sulfonate | |

Photoresist formulation compositions for Comparative Examples 1, 2 and Example 1 are shown in Table 3 below:

TABLE 3

| Sample | PAG | PAG (wt %) | Base (wt %) | SLA (wt %) |
|---|---|---|---|---|
| Comparative Example 1 | Comparative PAG 1 | 9.59 | 1.03 | 0.1 |
| Comparative Example 2 | Comparative PAG 2 | 9.97 | 1.03 | 0.1 |
| Example 1 | PAG-A1 | 13.03 | 1.03 | 0.1 |

The above photoresists were lithographically processed as follows. The photoresist was spin coated onto a 200 mm silicon wafer having Silicon antireflective coating (XS110532AA/HMDS, SiARC, Dow Electronic Materials) and baked at 110° C. for 60 seconds, to form a resist film 100 nm in thickness. The photoresist was exposed with ArF excimer laser (193 nm) through a mask pattern targeting a line and space pattern (L/S pattern) having a line width of 90 nm and a pitch of 180 nm, using an ArF exposure apparatus ASML-1100 (manufactured by ASML), NA (numerical aperture)=0.75 under annular illumination with outer/inner sigma of 0.89/0.64 with focus offset/step 0.10/0.05. The wafers were post exposure baked (PEB) at 100° C. for 60 seconds followed by developing with 0.26 N aqueous tetramethylammonium hydroxide (TMAH) developer and subsequent water wash.

+/−10% of the target diameter normalized by the sizing energy. Mask Error Factor (MEF) was defined as the ratio of CD change on the resolved resist pattern to the relative dimension change on the mask pattern. Line width roughness (LWR) is the deviation in the width of a line measured over a given length. LWR is quantified as the 3σ deviation of the width.

The results from the lithographic evaluation of the above photoresist formulations using SiARC are reported in the following Table 4.

TABLE 4

| PAG | Eo | EL % | MEF | LWR |
|---|---|---|---|---|
| Comparative PAG 1 | 4.4 | 12.23 | 2.80 | 7.0 |
| Comparative PAG 2 | 3.0 | 12.10 | 2.72 | 7.0 |
| PAG-A1 | 7.0 | 21.34 | 1.58 | 7.8 |

As seen in Table 4, photoresist that comprise PAG-A1 exhibit improved lithographic performance in terms of slower photospeed, exposure latitude, and Mask Error Factor.

High exposure latitude (EL), which defined as a difference in exposure energy to print +/−10% of the target diameter normalized by the sizing energy, was obtained for photoresist containing PAG-A1 as shown in Table 4 compared to comparative PAG 1 and comparative PAG 2. Interestingly, formulation A that contains the PAG-A1 produced the lowest Mask Error Factor (MEF). This indicates that PAGs with large molecular size are critical for minimizing the ratio of CD change on the resolved resist pattern with the relative dimension change on the mask pattern. The smaller MEF values were obtained for photoresist A, containing PAG-A1.

What is claimed is:

1. An acid generator comprising a structure of the following Formula (I):

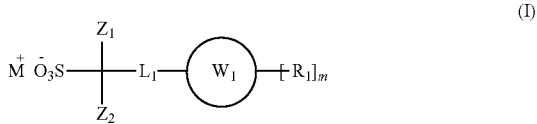

wherein:
M$^+$ is a counter ion;
$Z_1$ and $Z_2$ each independently represent a hydrogen or non-hydrogen substituent, where at least one of $Z_1$ or $Z_2$ is fluorine or fluoroalkyl;
$L_1$ is a linker group;
$W_1$ is an optionally substituted carbon alicyclic group or optionally substituted heteroalicyclic group;
$R_1$ is —(C=O)O(—(CXY)CX'Y'O)$_n$R where n is a positive integer, R is optionally substituted non-cyclic alkyl or, hydrogen and each X, Y, X' and Y' is a hydrogen or non-hydrogen substituent;
comprises one or more ether linkages; and
m is a positive integer.

2. The acid generator of claim 1 wherein $R_1$ is —(C=O)O(—CH$_2$CH$_2$O)$_n$R where n is a positive integer and R is non-cyclic alkyl or hydrogen.

3. The acid generator of claim 1 wherein $W_1$ is an optionally substituted heteroalicyclic group.

4. The acid generator of claim 1 wherein $W_1$ is an optionally substituted lactone.

5. The acid generator of claim 1 wherein $W_1$ is an optionally substituted carbon alicyclic group.

6. The acid generator of claim 1 wherein n is 1 or 2 and/or m is 1 or 2.

7. The acid generator of claim 1 wherein both $Z_1$ and $Z_2$ are fluorine or fluoroalkyl.

8. A photoresist composition comprising a resin and an acid generator of claim 1.

9. A method for providing a photoresist relief image comprising:
a) applying a coating layer of a photoresist of claim 8 on a substrate; and
b) exposing the photoresist composition layer to activating radiation and developing the exposed photoresist composition coating layer.

10. A photoresist composition comprising a resin and an acid generator of claim 2.

11. A photoresist composition comprising a resin and an acid generator of claim 3.

12. A photoresist composition comprising a resin and an acid generator of claim 4.

13. A photoresist composition comprising a resin and an acid generator of claim 5.

14. A photoresist composition comprising a resin and an acid generator of claim 6.

15. A photoresist composition comprising a resin and an acid generator of claim 7.

16. An acid generator of claim 1 wherein R is methyl or hydrogen.

17. An acid generator selected from the group consisting of:

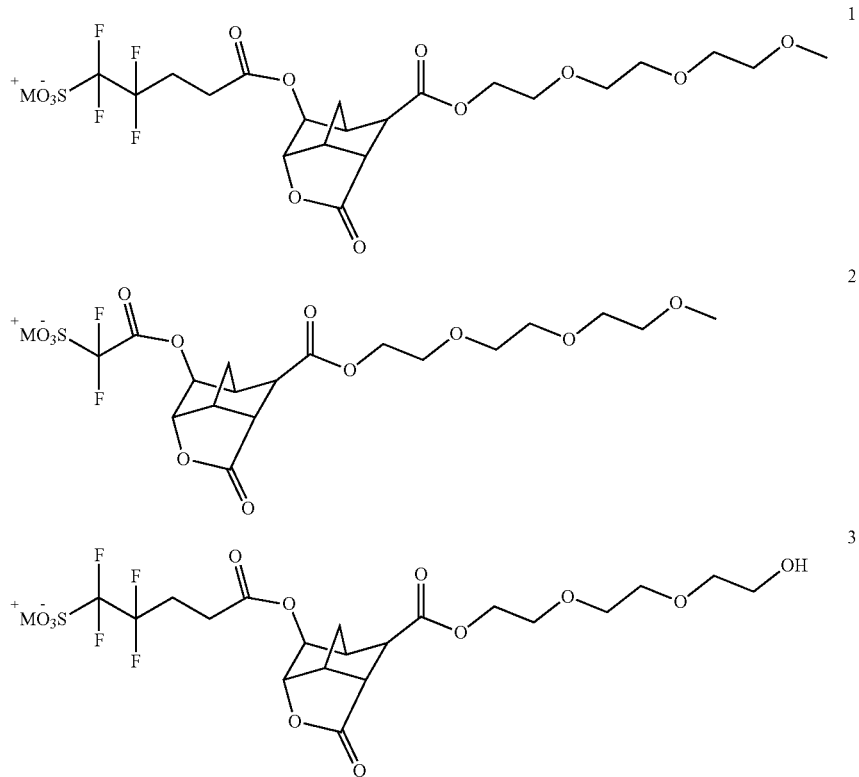

-continued
4
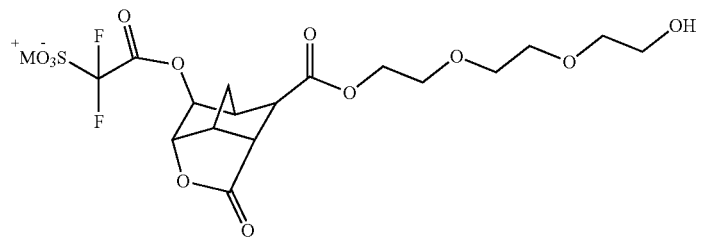
5
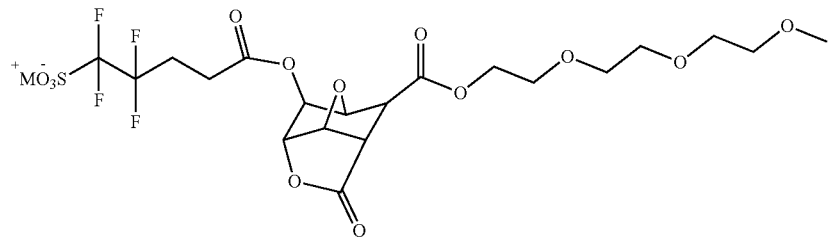
6
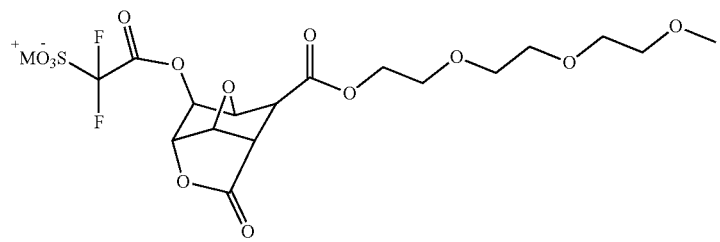
7
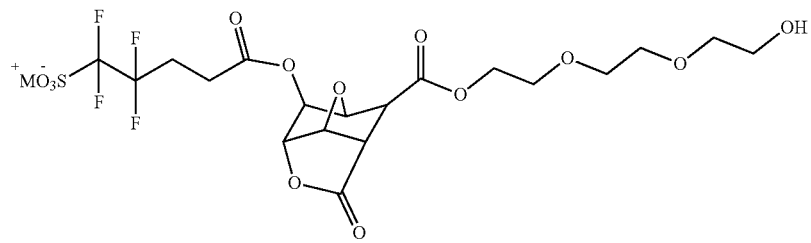
8
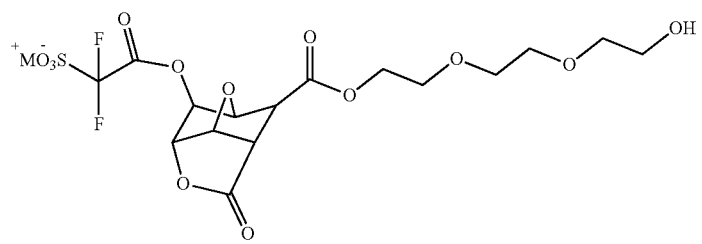
9
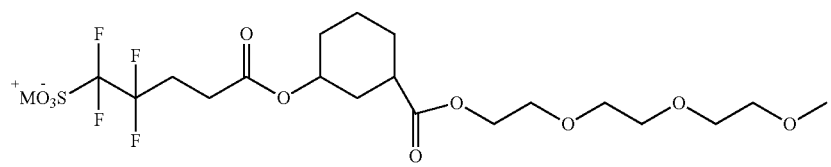
10
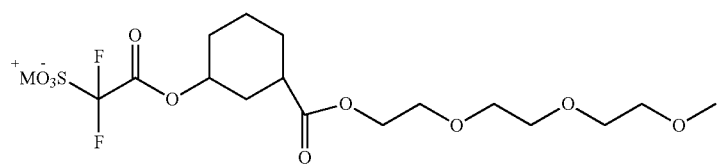

11
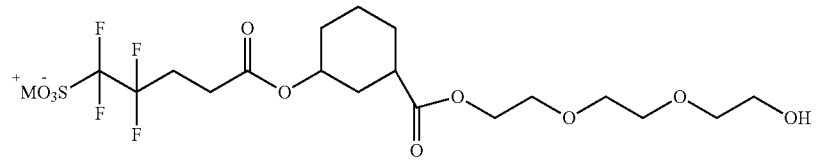
12
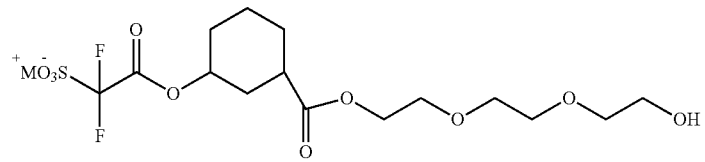
13
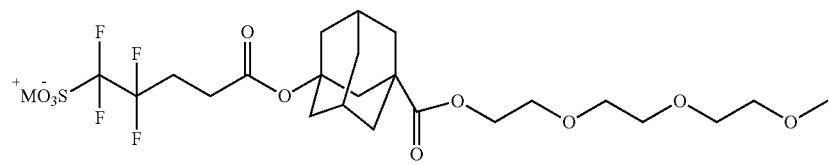
14
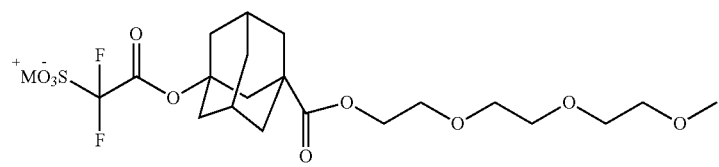
15
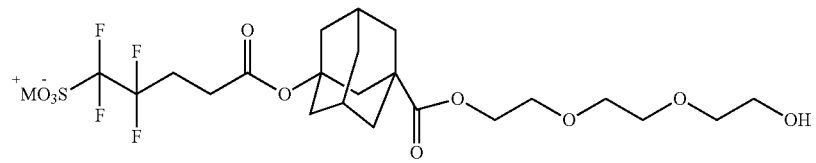
16
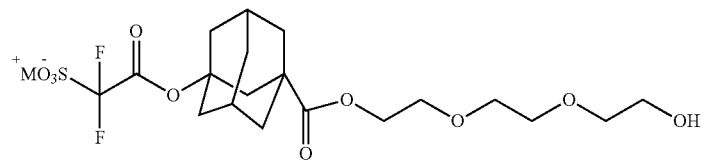
17
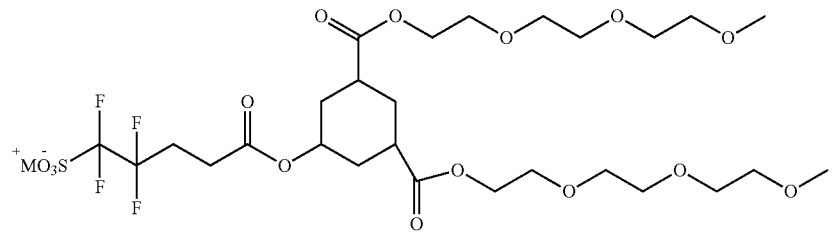
18
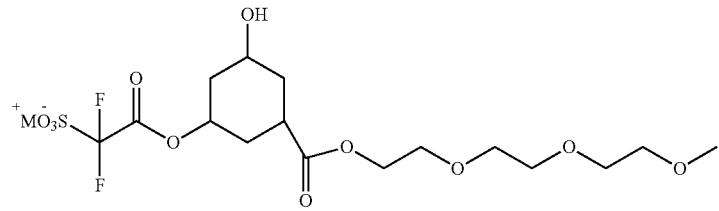

-continued
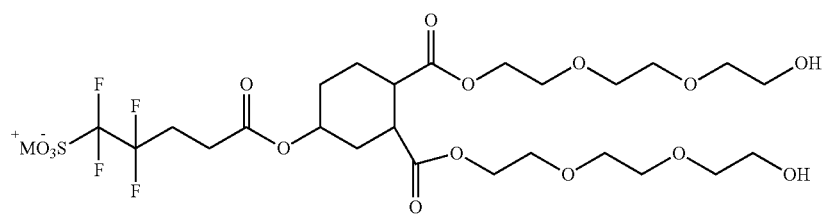
19
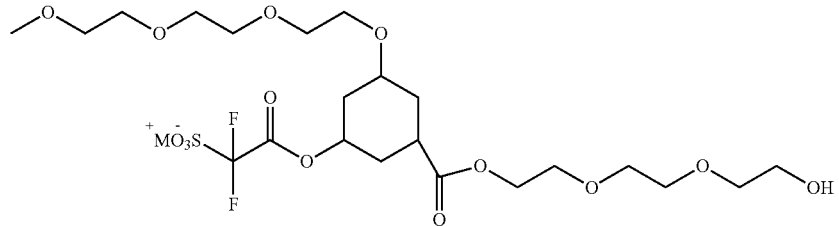
20
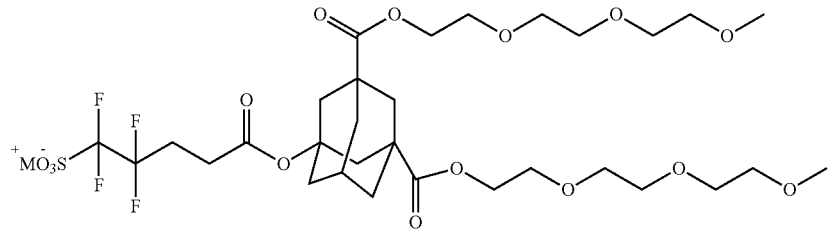
21
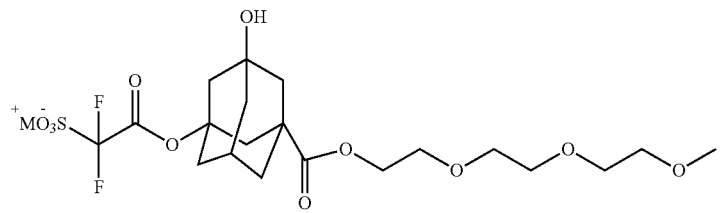
22
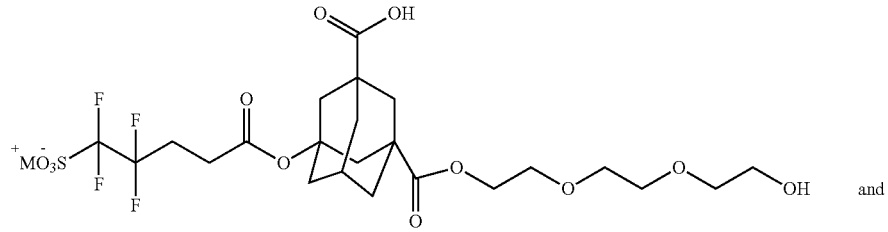
23 and
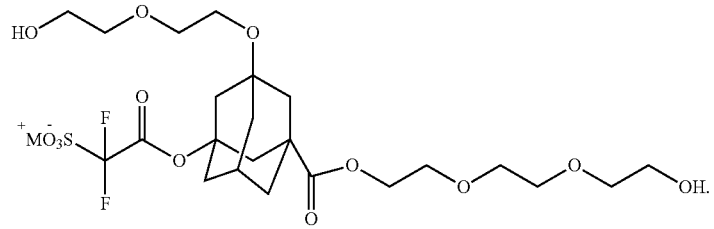
24
18. A photoresist composition comprising a resin and an acid generator of claim 17.
* * * * *